United States Patent [19]

Winter et al.

[11] 4,126,618
[45] Nov. 21, 1978

[54] ETHYL OR ACETYL DERIVATIVES OF 2-PYRIDYLMETHANETHIOL

[75] Inventors: Max Winter, Petit-Lancy; Fritz Gautschi, Commugny; Ivon Flament; Max Stoll, both of Petit-Lancy, all of Switzerland

[73] Assignee: Firmenich & Cie, Geneva, Switzerland

[21] Appl. No.: 874,736

[22] Filed: Feb. 3, 1978

Related U.S. Application Data

[60] Division of Ser. No. 615,748, Sep. 22, 1975, Pat. No. 4,085,109, which is a division of Ser. No. 482,819, Jun. 24, 1974, Pat. No. 4,038,435, which is a division of Ser. No. 243,866, Apr. 13, 1972, abandoned, which is a division of Ser. No. 70,560, Sep. 8, 1970, Pat. No. 3,702,253, which is a continuation-in-part of Ser. No. 543,069, Apr. 18, 1966, abandoned, which is a continuation-in-part of Ser. No. 452,342, Apr. 30, 1965, abandoned.

[51] Int. Cl.² ........................................... C07D 213/32
[52] U.S. Cl. ........................................... 546/339; 546/340; 546/261
[58] Field of Search .................. 260/294.8 E, 294.8 G, 260/294.8 R, 294.8 D

[56] References Cited

U.S. PATENT DOCUMENTS

| | | | |
|---|---|---|---|
| 2,607,775 | 8/1952 | Vinton | 260/294.8 G |
| 2,607,776 | 8/1952 | Vinton | 260/294.8 G |

*Primary Examiner*—Alan L. Rotman
*Attorney, Agent, or Firm*—Howard J. Newby; Thomas V. Sullivan; Bruno P. Struzzi

[57] ABSTRACT

Pyridine sulfur compounds of the formula:

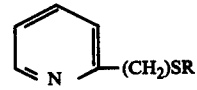

wherein R is ethyl or acetyl which are useful as flavor additives for foodstuffs and beverages.

3 Claims, No Drawings

ETHYL OR ACETYL DERIVATIVES OF 2-PYRIDYLMETHANETHIOL

This is a division of application Ser. No. 615,748 filed Sept. 22, 1975, now U.S. Pat. No. 4,085,109, issued April 4, 1978, which is a division of application Ser. No. 482,819 filed June 24, 1974, now U.S. Pat. No. 4,038,435, issued July 26, 1977, which is a division of application Ser. No. 243,866 filed April 13, 1972, and now-abandoned, which is a division of application Ser. No. 70,560 filed Sept. 8, 1970, now U.S. Pat. No. 3,702,253; which latter application is a continuation of now-abandoned application Ser. No. 543,069 filed Apr. 18, 1966, which is a continuation-in-part of now abandoned application Ser. No. 452,342 filed Apr. 30, 1965.

The invention relates to flavor agents in general. More particularly the invention relates to chemical compounds or compositions which have been found to have utility in the alteration of flavor or flavor characteristics of substances, whether naturally occurring or synthetic. Still more particularly the invention relates to a group of chemical compounds which have been found to be useful in the area of flavor-note alteration, whether by the enhancement of flavors or flavor-notes that are characteristic in a substance, by the alteration of a flavor or a flavor-note from a less to a more desirable one, or by the complete or partial masking of a flavor or flavor-note.

As is generally recognized by those familiar with the art, the science of flavor technology is an extremely complex one. Although much is known about flavor and flavor technology there is still a great deal to be learned in the field and the body of scientific literature is being rapidly expanded by those working in the area. The technology of flavor synthesis and blending of various flavor elements to achieve certain desirable results is of great commercial importance at the present stage of industrial advance. Commercial production of consumer goods from synthetic starting materials is becoming more and more common, and desirable, as world population continues to increase its demands upon the finite capacity for the production of natural products. Industry is also continually seeking means of upgrading natural products — methods of altering or enhancing the qualities of taste of less desirable natural products — usually more abundant — into more desirable product qualities. Often, for example, a product can be made commercially attractive only by masking or blanking out an undesirable flavor component. Formerly, before the advent of the flavor chemist and his technology, this unit of production would have been lost, or at least, would have had to have been re-processed to a useable quality. By the use of specifically designed flavoring agents, however, the undesirable flavor note can be eliminated or masked with another desirable one, and the expensive and time-consuming re-processing step eliminated or the production batch saved for use. Too, it is common in some segments of the industry, particularly the food industry, to add flavor agents to production units to enhance or bring out a desirable flavor characteristics of products — and by so doing to render the product more desirable from a consumer preference standpoint.

It is the object of this invention therefore, to provide the flavor technologist with additional tools for his use in the alteration of food flavors, whether it be flavor or flavor-note alteration generally or the enhancement or improvement of flavor or flavor notes specifically.

It is a further object of the invention to furnish a group of chemical compositions which have utility in the technology of flavor alteration, whether added to solid or liquid compositions for human consumption, and which may be used in either solid or liquid form.

A further object of the invention is to describe several groups of chemical compounds having desirable utility as flavor agents which may be prepared synthetically, thus enabling the food technologist to alter or enhance his product without drawing upon a natural product for the flavor agent.

A still further object of the invention is to describe a group of chemical compounds capable of synthesis from readily available organic substances which may be used singly or in combination to alter the flavor or flavor notes of compositions for food use, whether used in micro-quantities such as parts-per-million or in larger quantities, as the dictates of the end results may require.

Other objects will become apparent to those skilled in the art as the description proceeds.

Thus, in accordance with the concept of the instant invention, there is set out below a series of groups of compounds which have been found to have utility as flavor agents and to represent valuable materials to the food technologist who wishes to alter the flavor components of foods or food products either liquid foods or beverages, such as fruit and vegetable juices, milk, coffee, tea, cocoa, chocolate, and the like or solid foods such as cereals, flours, confections, vegetables, meats, etc. The flavor agents may be used either in liquid or solid form and are used in quantities designed to give the desired results, as will be more clearly explained as the description proceeds.

The chemical compounds which have been found to have utility as flavor agents may be generally classified according to the following groups:

I. — Diphenyls
II. — Substituted Naphthalenes
III. — Furan Hydrocarbons
IV. — Thiophene Hydrocarbons
V. — Pyrrole Hydrocarbons
VI. — Pyridine Hydrocarbons
VII. — Pyrazine Hydrocarbons
VIII. — Aliphatic and Aromatic Alcohols
IX. — Furan Ethers
X. — Thiophene Ethers
XI. — Thiazole Alcohols
XII. — Pyridine Ethers and Alcohols
XIII. — Pyrazine Ethers and Alcohols
XIV. — Benzofuran Carbonyl Compounds
XV. — Thiophene Aldehydes
XVI. — Pyrrole Aldehydes
XVII. — Pyrazine Carbonyl Compounds
XVIII. — Aliphatic and Aromatic Ketones
XIX. — Furan Ketones
XX. — Thiophene Ketones
XXI. — Pyrrole Ketones
XXII. — Thiazole Carbonyl Compounds
XXIII. — Pyridine Carbonyl Compounds
XXIV. — α-Diketones
XXV. — Thiophene-α-diketones
XXVI. — Pyrrol-α-diketones
XXVII. — Furan Esters
XXVIII. — Thiophene Esters
XXIX. — Pyridine Esters XXX. — Aromatic Sulfur Compounds
XXXI. — Furan Sulfur Compounds
XXXII. — Thiophene Sulfur Compounds
XXXIII. — Pyridine Sulfur Compounds
XXXIV. — Pyrrole Sulfur Compounds
XXXV. — Pyrazine Sulfur Compounds
XXXVI. — Phenols and Phenol Ethers
XXXVII. — Aliphatic Oxoalcohols
XXXVIII. — Miscellaneous The above groupings are selected more for reasons of chemical similarity than because of flavor alteration characteristics as will be more specifically described in relation to the more complete definition afforded each particular group.

The flavor agents or flavor modifying compositions of this invention are available to the food technologists in a variety of forms. It is usually preferable to use the agents in the form of a solution, for ease of dilution, exactitude of measurement, efficiency of distribution in the end use, etc. However the chemical nature of the compound, its solubility in acceptable solvents, its stability, and other characteristics may dictate the form in which it is used.

The amounts of the agents used is also subject to wide variation, of course. More concentrated materials, and those with the greatest degree of flavor modifying ability will be used in lesser amounts. Some degree of experimentation is, of course, required to achieve the desired results. A small, but flavor modifying amount, of the agents is blended with the material whose total flavor is to be altered, the amount depending upon the end result desired.

Two different types of methods were used in testing the compounds listed in this specification for their utility as flavor agents, flavor modifiers, flavor alteration agents, flavor-note enhancers, and the like. The first type method (A) served the purpose of determining the intrinsic taste, flavor and aroma of each individual compound. The second type methods (B) and (C) were used for testing the flavor- and aroma-modifying or -enhancing effects of the compounds hereinafter listed on coffee products and more particularly on spray-dried soluble coffee products commercially known as "instant coffee".

METHOD A

The vehicle used for testing the flavor compounds was a 65% solution of cane sugar in tap water. The flavor compounds were incorporated in this sugar syrup in the form of 1% or 1 per 1000 by weight solutions in 96% ethyl alcohol. The concentration of the flavor compounds in the sugar syrup varied between about 0.005 and 5 g. for 100 liters of syrup according to the varying strength of flavor compounds. Samples of each flavored sugar syrup were submitted to the members of the tasting panels. After tasting the samples each member had to give an evaluation of each flavor compound in terms of descriptive words.

In the evaluation of materials for the alteration or enhancement of coffee flavor or of coffee flavor notes it is essential that the equipment used, coffee pots, cups, spoons, measuring equipment, etc. be absolutely clean prior to use.

METHOD B

The coffee base was prepared by dissolving 1 g. of a commercial spray-dried soluble coffee in boiling water. A sufficient number of pots was prepared to provide one pot for each flavor agent to be evaluated plus one control. The flavor agent was added to the coffee base in the form of a 1% or 1 per 1000 by weight alcoholic solution at concentrations varying between 0.005 and 5 g. of flavor agent for 100 liters of coffee base. The measured quantity of the flavor agent was added to a pot of the coffee base material, stirred well, and poured immediately into cups for the organoleptic evaluation. The taste tests were made within a short time (not more than 15 minutes) after the final composition to be tested was prepared.

The organoleptic evaluation involved grading a series of cups that were coded, the taster merely rating the coded cups against the standard or control which did not contain the flavor agent. The standard was placed at the first position in a series of cups. The tasters were asked to ascertain whether or not there existed differences in the flavor of the samples to be tested as compared with the control. The tasters were furthermore asked to describe and characterize the various flavor notes and types determined.

METHOD C

Using boiling Crystal Spring Water, to provide a clean starting taste, a 1.35% solution of relatively bland tasting commercially available spray-dried soluble coffee was prepared. The containers used — preferably the lower portion of a glass coffee maker — was absolutely clean, as was the other equipment used, e.g. cups and spoons.

A sufficient number of containers, or pots, were used to accomodate each flavor fraction to be studied, plus one control. The flavor fraction was measured carefully with a micro-syringe, adding from 2 to 150 microliters of the flavor fraction per pot. The mixture of coffee solution and flavor fraction was stirred and immediately poured into cups for tasting. At least 5 experienced tasters are used. The tasting should begin at least within 15 minutes after the solution is prepared. If not, the solution should be discarded and fresh solution prepared.

The cups are coded and the samples are not identified. A standard sample is included in which no flavor fraction has been added. The taster is asked to identify and describe the flavor enhancement or modification noted.

In the following specific description of the compounds of the Groups listed above (I–XXXVIII) there is first given the structural formula followed by a list of members of the group which have been found to have outstanding utility in the concept of this invention. Immediately following the chemical name of each member there is given the commercial source or a literature reference giving a method for its preparation. Commercially available products will be identified by the abbreviation c.a., and may be obtained from FLUKA, A.G., Buchs S.G., Switzerland; ALDRICH CHEM. CO., Milwaukee, Wis.; DR. F. RASCHIG GMBH, Ludwigshafen a. Rh., West-Germany; or K & K LABORATORIES INC., Plainview, NY. 11803.

In those instances wherein new compounds are described a detailed method of preparation is given following the list of the group members. New compounds will be identified by the abbreviation n.c.

The results of the organoleptic evaluation tests are set out in the group of TABLES following the detailed description of the groups of compounds.

I. — DIPHENYLS

In this first group of compounds are included those having the structural formula:

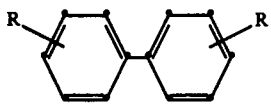
(1)

wherein R is hydrogen or an alkyl group, e.g. methyl.
Typical compounds are:

| (1) | a. | diphenyl | c.a. |
|---|---|---|---|
|  | b. | 2-methyl-diphenyl | c.a. |
|  | c. | 3-methyl-diphenyl | c.a. |
|  | d. | 4-methyl-diphenyl | c.a. |
|  | e. | 4,4'-dimethyl-diphenyl | c.a. |

Organoleptic evaluations as flavor agents are described in TABLE I below.

II. — SUBSTITUTED NAPHTHALENES

Compounds in this group are those having the general formula:

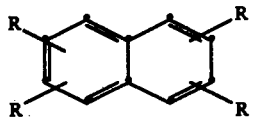
(1)

wherein R is hydrogen or an alkyl group, e.g. methyl or ethyl, at least one of the R's being an alkyl group.
Typical compounds include:

| (1) | a. alpha-methyl-naphthalene | c.a. |
|---|---|---|
|  | b. beta-methyl-naphthalene | c.a. |
|  | c. beta-ethyl-naphthalene | c.a. |
|  | d. 1,2-dimethyl-naphthalene | c.a. |
|  | e. 1,3-dimethyl-naphthalene | c.a. |
|  | f. 1,4-dimethyl-naphthalene | c.a. |
|  | g. 1,5-dimethyl-naphthalene | c.a. |
|  | h. 1,6-dimethyl-naphthalene | c.a. |
|  | i. 2,3-dimethyl-naphthalene | c.a. |
|  | j. 2,6-dimethyl-naphthalene | c.a. |
|  | k. 1,3,7-trimethyl-naphthalene | c.a. |
|  | l. 2,3,5-trimethyl-naphthalene | c.a. |
|  | m. 2,3,6-trimethyl-naphthalene | c.a. |
|  | n. alpha-ethyl-naphthalene | c.a. |
|  | o. 1,7-dimethyl-naphthalene | c.a. |
|  | p. 2,7-dimethyl-naphthalene | c.a. |

The compounds enumerated above were evaluated organoleptically and gave the results set out in TABLE II below.

III. — FURAN HYDROCARBONS

The compounds of this group which have utility according to the inventive concept are selected from the class of compounds having the general formula:

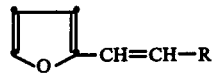
(1)

wherein R is hydrogen or an alkyl group containing from 1 to 3 carbon atoms;
compounds of the formula:

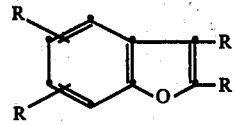
(2)

wherein R is hydrogen or an alkyl or an alkenyl group of from 1 to 3 carbon atoms, provided that the sum of the carbon atoms of the substituent groups does not exceed 3; and compounds of the formula:

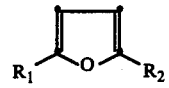
(3)

wherein $R_1$ is hydrogen or a methyl group and wherein $R_2$ is

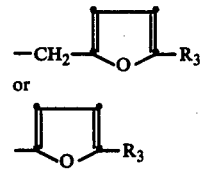

or $R_3$ being hydrogen or a methyl group such that $R_1$ and $R_3$ are not both hydrogen.

Specific compounds included in this group of compounds are:

| (1) | a. 2-vinyl-furan | Bull. 1947, 453 |
|---|---|---|
|  | b. 2-(1)-pentenyl-furan | C.A. 1961, 85905f |
| (2) | a. benzofuran | c.a. |
|  | b. 2-methyl-benzofuran | Soc. 1955, 3689 |
|  | c. 2-ethyl-benzofuran | J.A.C.S. 73,754 (1951) |
|  | d. 2,3-dimethyl-benzofuran | Soc. 1955, 3689 |
|  | e. 2-vinyl-benzofuran | J.A.C.S. 73, 754 (1951) |
|  | f. 2-isopropenyl-benzofuran | n.c. |
|  | g. 7-methyl-benzofuran | J.Chem.Soc.1920, 1534 |
|  | h. 7-ethyl-benzofuran | n.c. |
|  | i. 2,7-dimethylbenzofuran | n.c. |
| (3) | a. 2,2'-difuryl | J.A.C.S. 73, 1271 (1951) |
|  | b. 5-methyl-2,2'-difuryl-methane | C.A. 1957, 6594a |
|  | c. 5,5'-dimethyl-2,2'-difuryl-methane | Helv. 1932, 1068 |

The new compounds included in Group III can be prepared by the methods described below.

(2) f. 2-Isopropenyl-benzofuran. According to the method described in J.A.C.S. 73, 754 (1951) 2-acetyl-benzofuran is reacted with methyl-magnesium bromide to form 2-(2-hydroxyisopropyl)-benzofuran which is converted to its acetate. Pyrolysis of the acetate yields 2-isopropenyl-benzofuran of b.p. 81°–83° C./0.001 mm. Hg.

(2) h. 7-Ethyl-benzofuran is prepared by the method described in J.Chem.Soc. 1920, 1534, but using o-ethyl-phenol instead of o-cresol. The MS. of the product thus obtained shows the following ion peaks with the relative intensities given within brackets: 131 (100%), 146 (38%) and 77 (10%).

(2) i. 2,7-Dimethyl-benzofuran. 7-Methyl-benzofuran (of. compound (2) g.) is subjected to a WILSMEYER reaction to form 7-methyl-benzofuran-2-aldehyde which is converted into 2,7-dimethyl-benzofuran by a WOLFF-KISHNER reaction by the method described in Bull.Soc.Chim.France 29, 1875 (1952). The product thus obtained has the following peaks in its MS: 146 (100%), 145 (92%) and 131 (32%).

Organoleptic evaluations of this group of compounds are set out in TABLE III below.

IV. — THIOPHENE HYDROCARBONS

The thiophene hydrocarbons having utility in accordance with the instant inventive concept are those compounds described by the structural formula:

 (1)

wherein $R_1$ and $R_2$ are hydrogen, methyl, ethyl, vinyl or propyl, the compound of the formula:

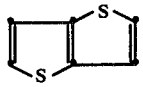 (2)

the compounds of the formula:

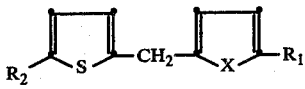 (3)

wherein $R_1$ and $R_2$ are hydrogen or methyl groups, and wherein X is oxygen or sulfur;

the compounds of the formula

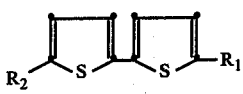 (4)

wherein $R_1$ and $R_2$ are hydrogen or methyl groups, and the compounds of the formula

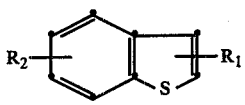 (5)

wherein $R_1$ and $R_2$ represent hydrogen or alkyl groups.

Typical compounds of this class of compounds are:

| | | |
|---|---|---|
| (1) | a. 2-methyl-thiophene | c.a. |
| | b. 3-methyl-thiophene | c.a. |
| | c. 2-ethyl-thiophene | c.a. |
| | d. 3-ethyl-thiophene | Bull. 1955, 424 |
| | e. 2-propyl-thiophene | J.A.C.S. 70, 391, Bull. 1955, 361 |
| | f. 2-vinyl-thiophene | Bull.1955, 424 |
| | g. 3-vinyl-thiophene | Bull. 1955, 424 |
| | h. 2-methyl-4-ethyl-thiophene | J.A.C.S.75,989 (1953) |
| | i. 2-methyl-5-ethyl-thiophene | J.A.C.S.75, 989 (1953) |
| | j. 2-methyl-5-propyl-thiophene | J.A.C.S.75, 989 (1953) |
| | k. 2,5-dimethyl-thiophene | c.a. |
| (2) | a. 2,3,3'-thiophenothiophene | Soc. 1953, 1837 |
| (3) | a. 2,2'-dithienyl-methane | J.A.C.S.73, 1270 (1951) |
| | b. 5,5'-dimethyl-2,2'-dithienyl-methane | J.A.C.S.73, 1270 (1951) |
| | c. 2-furyl-2-thienyl-methane | C.A. 57, 9776f(1962) |
| | d. (5-methyl-2-thienyl)-2-furyl-methane | C.A. 57, 9776f (1962) |
| (4) | a. 2,2'-dithienyl | J.A.C.S.78, 1958 (1956) |
| | b. 5,5'-dimethyl-2,2'-dithienyl-methane | J.A.C.S.78, 1958 (1956) |
| (5) | a. benzothiophene | c.a. |
| | b. 2-methyl-benzothiophene | J.A.C.S.74, 664 (1952) |

Organoleptic evaluations of these compounds are set out in TABLE IV below.

V. — PYRROLE HYDROCARBONS

Compounds of this group have the general formulae:

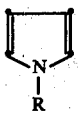 (1)

wherein R is alkyl, e.g. ethyl, amyl, isoamyl, or alphamethylbutyl, and

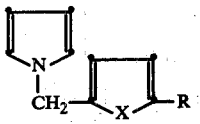 (2)

wherein X is oxygen or sulfur and R is hydrogen or a methyl group, provided that, if X represents oxygen, R is methyl.

Typical compounds of this group include:

| | | |
|---|---|---|
| (1) | a. 1-ethyl-pyrrole | Helv.10, 387 (1927) |
| | b. 1-n-amyl-pyrrole | Helv.10, 387 (1927) |
| | c. 1-isoamyl-pyrrole | Helv.10, 387 (1927) |
| | d. 1-(alphamethyl-butyl)-pyrrole | Helv.10, 387 (1927) |
| (2) | a. 1-(5-methyl-2-furfuryl)-pyrrole | n.o.; b.p.104° C./11 mm; prepared by the same method as (1) a. |
| | b. 1-thienyl-pyrrole | J.Org.Chem.28,574 (1963) |

Organoleptic test evaluations are set out in TABLE V below.

VI — PYRIDINE HYDROCARBONS

The compounds of this group which have utility according to the instant concept are to be described as falling under the general formula:

 (1)

wherein $R_1$, $R_2$ and $R_3$ are hydrogen, alkyl, e.g. methyl, ethyl, isobutyl; alkenyl groups, e.g. vinyl, propenyl; aryl groups; or aralkyl groups; provided that the symbols $R_1$, $R_2$ and $R_3$ are not all hydrogen.

Typical compounds include:

| | | |
|---|---|---|
| (1) | a. 2-methyl-pyridine | c.a. |
| | b. 3-methyl-pyridine | c.a. |
| | c. 3-ethyl-pyridine | c.a. |
| | d. 2-allyl-pyridine | Bull. 420, (1955) |
| | e. 4-isobutyl-pyridine | Bull. 420, (1955) |
| | f. 2-(1)-propenyl-pyridine | Ann. 247, 1 (1888) |
| (1) | g. 4-(1)-propenyl-pyridine | Ann. 247, 1 (1888) |
| | h. 2-methyl-5-ethyl-pyridine | c.a. |
| | i. 2,3-dimethyl-pyridine | c.a. |
| | j. 2,4-dimethyl-pyridine | c.a. |
| | k. 2,5-dimethyl-pyridine | c.a. |
| | l. 2,6-dimethyl-pyridine | c.a. |
| | m. 3,4-dimethyl-pyridine | c.a. |
| | n. 3,5-dimethyl-pyridine | c.a. |
| | o. 2-vinyl-pyridine | c.a. |
| | p. 4-methyl-pyridine | c.a. |
| | q. 2-methyl-6-vinyl-pyridine | c.a. |
| | r. 4-phenyl-pyridine | c.a. |
| | s. 4-benzyl-pyridine | c.a. |

| | |
|---|---|
| t. 2-benzyl-pyridine | c.a. |
| u. 2-methyl-5-ethyl-pyridine | c.a. |

Organoleptic evaluations are set out in TABLE VI below.

VII — PYRAZINE HYDROCARBONS

This important group of compounds have been found to have exceptional utility as flavor agents in accordance with the instant inventive concept. Compounds of the group have the general formulae:

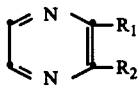  (1)

wherein $R_1$ is hydrogen, alkyl, 1-pyrrolyl or 2-thienyl; and $R_2$ is alkyl or alkenyl,

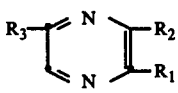  (2)

wherein $R_1$, $R_2$ and $R_3$ are alkyl groups having from 1 to 5 carbon atoms,

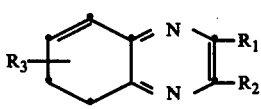  (3)

wherein $R_1$, $R_2$ and $R_3$ are hydrogen or methyl groups,

  (4)

wherein $R_1$ and $R_2$ are alkyl groups containing from 1 to 3 carbon atoms,

  (5)

wherein $R_1$, $R_2$, $R_3$ and $R_4$ are alkyl groups containing from 1 to 6 carbon atoms, and

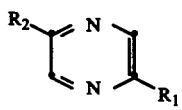  (6)

wherein $R_1$ is methyl or ethyl and $R_2$ is alkyl or alkenyl with $C_1$ to $C_6$.

Compounds of this group which are of special interest include:

| | | |
|---|---|---|
| (1) | a. 2-methyl-3-ethyl-pyrazine | n.c. |
| | b. 2-methyl-3-isobutyl-pyrazine | n.c. |
| | c. 2-methyl-3-propyl-pyrazine | n.c. |
| | d. 2-methyl-3-isopropyl-pyrazine | n.c. |
| | e. 2-methyl-3-butyl-pyrazine | n.c. |
| | f. 2-methyl-3-amyl-pyrazine | n.c. |
| | g. 2-methyl-3-hexyl-pyrazine | n.c. |
| | h. 2,3-dimethyl-pyrazine | Ber. 40, 4855 (1907) |
| | i. 2,3-diethyl-pyrazine | n.c. |
| | j. 2-ethyl-3-vinyl-pyrazine | n.c. |
| | k. 2-methyl-3(5,6)-(pyrrolyl-1)-pyrazine | n.c. |
| | l. 2-methyl-3-(thienyl-2)-pyrazine | n.c. |
| | m. 2-ethyl-pyrazine | J.Org.Chem.26, 3379 (1961) |
| | n. 2-propyl-pyrazine | J.Org.Chem.26, 3379 (1961) |
| | o. 2-isopropyl-pyrazine | J.Org.Chem.26, 3379 (1961) |
| | p. 2-vinyl-pyrazine | J.Org.Chem.26, 3379 (1961) |
| | q. 2-isopropenyl-pyrazine | n.c. |
| | r. 2-methyl-3-vinyl-pyrazine | n.c. |
| (2) | a. trimethyl-pyrazine | J.A.C.S. 72, 844(1950) |
| | b. 2,6-dimethyl-3-ethyl-pyrazine | n.c. |
| | c. 2,5-dimethyl-3-ethyl-pyrazine | n.c. |
| | d. 2,5-dimethyl-3-propyl-pyrazine | n.c. |
| | e. 2,6-diethyl-3-methyl-pyrazine | n.c. |
| | f. 2,5-diethyl-3-methyl-pyrazine | n.c. |
| | g. 2,5-dimethyl-3-butyl-pyrazine | n.c. |
| | h. 2,3-dimethyl-5-isoamyl-pyrazine | n.c. |
| | i. 2,5-dimethyl-3-isoamyl-pyrazine | n.c. |
| | j. 2,3-diethyl-5-methyl-pyrazine | n.c. |
| (3) | a. 5-methyl-quinoxaline | Ann.237, 336 (1887) |
| | b. 2-methyl-quinoxaline | Org. Synth.30,86 (1950) |
| | c. 6-methyl-quinoxaline | Ann. 237, 336 (1887) |
| | d. 2,3-dimethyl-quinoxaline | Ber. 40, 4832 (1907) |
| | e. 2-methyl-3-ethyl-quinoxaline | Ber. 32, 526 (1889) |
| | f. 2,3-diethyl-quinoxaline | J.A.C.S.79,1712 (1957) |
| (3) | g. 2-methyl-3-propyl-quinoxaline | J.Chem.Soc. 1946, 54 |
| | h. 2-methyl-3-isopropyl-quinoxaline | J.Chem.Soc. 1953, 2822 |
| | i. 2-methyl-3-butyl-quinoxaline | n.c. |
| | j. 2-methyl-3-isobutyl-quinoxaline | n.c. |
| | k. 2-methyl-3-amyl-quinoxaline | J.Chem.Soc. 1943, 322 |
| | l. 2-ethyl-quinoxaline | J.Chem.Soc. 1953, 2822 |
| (4) | a. 2-methyl-6-ethyl-pyrazine | n.c. |
| | b. 2-methyl-6-propyl-pyrazine | J.Org.Chem. 27, 1355 (1962) |
| | c. 2,6-diethyl-pyrazine | n.c. |
| | d. 2-methyl-6-vinyl-pyrazine | n.c. |
| (5) | a. trimethyl-butyl-pyrazine | n.c. |
| | b. trimethyl-isoamyl-pyrazine | n.c. |
| | c. 2,5-dimethyl-3,6-dipropyl-pyrazine | n.c. |
| | d. 2,5-dimethyl-3,6-diisopropyl-pyrazine | n.c. |
| | e. 2,5-dimethyl-3,6-dibutyl-pyrazine | n.c. |
| | f. 2,5-dimethyl-3,6-diisobutyl-pyrazine | n.c. |
| | g. 2,5-dimethyl-3,6-diamyl-pyrazine | n.c. |
| | h. 2,5-dimethyl-3,6-dihexyl-pyrazine | n.c. |
| | i. 2,3,5-trimethyl-6-hexyl-pyrazine | n.c. |
| | j. 2,5-dimethyl-3,6-diethyl-pyrazine | n.c. |
| (6) | a. 2-ethyl-5-methyl-pyrazine | n.c. |
| | b. 2-isopropyl-5-methyl-pyrazine | n.c. |
| | c. 2,5-diethyl-pyrazine | n.c. |
| | d. 2-methyl-5-vinyl-pyrazine | n.c. |

Organoleptic evaluations are set out in TABLE VII below

The new compounds of this Group VII can be prepared as follows:

The 2,3-disubstituted pyrazines (formula (1)) can be obtained by a method comprising catalytically dehydrogenating with copper chromite the correspondingly substituted dihydropyrazines which, in turn, can be prepared by condensation of ethylene diamine with the corresponding alpha-diketones. By way of illustration the preparation of 2-methyl-3-ethyl-pyrazine is described in more details.

(1) a. 2-Methyl-3-ethyl-pyrazine. In a 3-necked flask equipped with a stirrer, means for cooling and a dropping funnel there was placed 150 g. of ethylene diamine in 500 ml. ether. After cooling to 0° C. there was slowly added with stirring a solution of 250 g. of ethyl methyl diketone in 500 ml. of ether. After the addition was complete, the temperature was allowed to rise to room temperature and the mixture was heated on a water bath for a few minutes. The material separated into 2 phases and the water phase was discarded. The ether phase was dried with sodium sulfate, the solvent was removed by evaporation and the residue distilled under reduced pressure and an inert atmosphere. There was obtained 192 g. of the dihydropyrazine (62% yield), boiling point 61°–65° C./11 mm. Hg.

In an apparatus similar to that described by Bouveault in Bull IV, 3, 119 (1908) the dihydro pyrazine was distilled under reduced pressure under nitrogen atmosphere through a column containing copper chromite (Girdler G-13). The catalyst was heated to 300° C. electrically and the effluent was passed through a Widmer column to separate the unhydrogenated material.

The product was condensed, dried and redistilled; a 90% yield was obtained of a product boiling at 57° C./10 mm.Hg.

The same method as used for compound (1) a. was applied for the preparation of the following compounds:

| | |
|---|---|
| (1) b. 2-methyl-3-isobutyl-pyrazine | b.p.74° /10 mm. Hg. |
| (1) c. 2-methyl-3-propyl-pyrazine | b.p. 71° –72° /10 mm. Mg. |
| (1) d. 2-methyl-3-isopropyl-pyrazine | b.p. 59° /10 mm. Hg. |
| (1) e. 2-methyl-3-butyl-pyrazine | b.p. 83° –84° /9 mm. Mg. |
| (1) f. 2-methyl-3-amyl-pyrazine | b.p. 98° /10 mm. Hg. |
| (1) g. 2-methyl-3-hexyl-pyrazine | b.p. 113° –115° /9 mm. Hg. |
| (1) i. 2,3-diethyl-pyrazine | b.p. 69° –71° /12 mm. Mg. |

(1) j. 2-Ethyl-3-vinyl-pyrazine can be prepared from 2-ethyl-3-methyl-pyrazine by the method described in J. Org. Chem. 27, 1363 (1962). B.p. 75°–80° C./10 mm.Hg.

(1) k. 2-Methyl-3(5,6)-(pyrrolyl-1)-pyrazine can be prepared as follows: N-Pyrrolyl-lithium is prepared by reacting 0.242 mole (15.4 g.) of butyllithium (as 15% suspension in hexane) with 0.22 mole (14.7 g.) of pyrrole at −20° C. in the presence of 100 ml. of tetrahydrofuran. There is then added at room temperature a solution of 0.2 mole (25.6 g.) of 3(5,6)-chloro-2-methyl-pyrazine [obtained by the method described in J. Org. Chem. 26, 2356 (1961)] in 75 ml. of tetrahydrofuran. The reaction mixture is refluxed for 5 days and subjected to the usual treatments for purifying and isolating the reaction product which is then distilled. There is thus obtained 2-methyl-3(5,6)-N-pyrrolyl-pyrazine as a fraction distilling at 120°–124° C./10 Torr.

(1) 1. 2-(Thienyl-2)-3-methyl-pyrazine is prepared as follows. A solution of 0.36 g. (0.006 mole) of ethylene diamine in 3 ml. of ether is cooled to 0° C. To this solution there is added slowly in a nitrogen atmosphere a solution of 0.94 g. (0.006 mole) of (thienyl-2) methyl diketone (obtained by oxidation of 2-propionylthiophene with selenium dioxide) in 3 ml. of absolute ether. The ether is gradually replaced by benzene, and water is removed as an azeotropic mixture with the latter solvent. The reaction product is fractionally distilled, and the fraction boiling at 85°–105° C./0.003 mm. Hg. is redistilled through a copper chromite column (GIRDLER G-13) heated at 350° C. There is thus obtained 2-(thienyl-2)-3-methyl-pyrazine of b.p. 94° C./0.03 mm. Hg.

(1) q. 2-Isopropenyl-pyrazine is obtained from 2-ethylpyrazine by the method described in J.Org.Chem. 27, 1363 (1962). It has the following peaks in the MS: 119 (100%), 120 (81%) and 67 (21%).

(1) r. 2-Methyl-3-vinyl-pyrazine is prepared from 2,3-diethylpyrazine by the same method as used for compound (1) q. It has a b.p. of 66°–67° C./13 mm. Hg.

(2) b. 2,6-Dimethyl-3-ethyl-pyrazine is prepared by the addition of an ethyl group at the 3-position of 2,6-dimethylpyrazine by the alkyl-lithium method described by Klein et al. in J.A.C.S. 73, 2949 (1951). The resulting product has a b.p. of 64°–66° C./8 mm. Hg.

(2) c. 2,5-Dimethyl-3-ethyl-pyrazine is prepared by the addition of an ethyl group at the 3-position of 2,5-dimethyl-pyrazine by the alkyl-lithium method described by Klein et al. (loc.cit.). The resulting product has a b.p of 63°–68° C./8 mm. Hg.

(2) d. 2,5-Dimethyl-3-propyl-pyrazine is prepared by the addition of an n-propyl group at the 3-position of 2,5-dimethylpyrazine by the alkyl-lithium method described by Klein et al. (loc.cit.). The product is identified by mass spectrometry. It has a b.p. of 80° C./10 mm. Hg.

(2) e. 2,6-Diethyl-3-methyl-pyrazine is prepared by the introduction of a methyl group into the 3-position of 2,6-diethylpyrazine by the method of Klein et al. (loc.cit.). The product has a b.p. of 91°–92° C./13 mm. Hg.

(2) f. 2,5-Diethyl-3-methyl-pyrazine is prepared by the introduction of a methyl group into the 3-position of 2,5-diethylpyrazine by the method of Klein et al. (loc.cit.). The product was isolated by gas chromatography and was identified by mass spectrometry.

(2) g. 2,5-Dimethyl-3-butyl-pyrazine is prepared by introducing a butyl group into the 3-position of 2,5-dimethylpyrazine by the method of Klein et al. (loc.cit.). The resulting product has a b.p. of 91° C./9 mm. Hg.

(2) h. 2,3-Dimethyl-5-isoamyl-pyrazine is prepared by introducing an isoamyl group into the 5-position of 2,3-dimethylpyrazine by the method of Klein et al. (loc.cit.). The product is identified by mass spectrometry.

(2) i. 2,5-Dimethyl-3-isoamyl-pyrazine is prepared by introducing an isoamyl group into the 3-position of 2,5-dimethylpyrazine by the method of Klein et al. (loc.cit.). The product has a b.p. of 110°–120° C./13 mm. Hg.

(2) j. 2,3-Diethyl-5-methyl-pyrazine is prepared by the method described for the preparation of compound (1) a. in Group VII, using 1,2-diamino-propane instead of ethylene diamine and dipropionyl as the α-diketone. The product has a b.p. of 79°–80° C./12 mm. Hg.

(3) i. 2-Methyl-3-butyl-quinoxaline is obtained by the same method as compound (3) d. of Group VII. It has a b.p. of 153° C./9 mm. Hg.

(3) j. 2-Methyl-3-isobutyl-quinoxaline is obtained by the same method as compound (3) e. of Group VII. It has a m.p. of 94°–95° C.

(4) a. 2-Methyl-6-ethyl-pyrazine was obtained by the alkylation of 2,6-dimethyl-pyrazine by the method described by Levine and Behun in J.Org.Chem. 26, 3379 (1961). It has a boiling point of 54°–57° C./11 mm. Hg.

(4) c. 2,6-Diethyl-pyrazine was obtained by subjecting compound (4) a. to a second alkylation by the procedure described above. It has a boiling point of 70° at 10 mm. Hg.

(4) d. 2-Methyl-6-vinyl-pyrazine is obtained by starting with 2,6-dimethyl-pyrazine and following the method of Levine et al. reported by J.Org.Chem. 27, 1363 (1962). It has a b.p. of 74°–75°/22 mm. Hg.

(5) a. 2,3,5-Trimethyl-6-butyl-pyrazine was prepared by introducing a butyl group into the 6-position of 2,3,5- trimethylpyrazine by the method of Klein et al. (loc.cit.). The product was isolated by gas chromatography and identified by mass spectrometry.

(5) b. 2,3,5-Trimethyl-6-isoamyl-pyrazine was prepared by introducing an isoamyl group into the 6-position of 2,3,5-trimethyl-pyrazine by the method of Klein et al. (loc.cit.). The product had a b.p. of 80° C./10 mm.Hg.

(5) c. 2,5-Dimethyl-3,6-dipropyl-pyrazine was prepared by first forming 3-oximino-2-hexanone by reacting 2-hexanone with nitrosyl chloride according to the method of BOUVEAULT, Bull. [3] 31, 1163 (1904). The autocondensation of two molecules of the imino-ketone in the presence of zinc and acetic acid [according to the method described in Chimia 11, 310 (1957)] yielded 2,5-dimethyl-3,6-dipropyl-pyrazine which had a b.p. of 109°-110° C./10 mm. Hg.

(5) d. 2,5-Dimethyl-3,6-diisopropyl-pyrazine was prepared by first forming 4-methyl-3-oximino-2-pentanone by reacting 4-methyl-2-pentanone with nitrosyl chloride according to the method of BOUVEAULT, Bull. [3] 31, 1163 (1904). The autocondensation of two moles of the imino-ketone in the presence of zinc and acetic acid [according to the method described in Chimia 11, 310 (1957)] yielded 2,5-Dimethyl-3,6-diisopropyl-pyrazine which had a b.p. of 91° C./8 mm. Hg.

(5) e. 2,5-Dimethyl-3,6-dibutyl-pyrazine was prepared by first forming 3-oximino-2-heptanone by reacting 2-heptanone with nitrosyl chloride according to the method of BOUVEAULT, Bull. [3] 31, 1163 (1904). The autocondensation of two moles of the imino-ketone in the presence of zinc and acetic acid [according to the method described in Chimia 11, 310 (1957)] yielded 2,5-dimethyl-3,6-dibutyl-pyrazine which had a b.p. of 18° C./0.002 mm. Hg.

(5) f. 2,5-Dimethyl-3,6-diisobutyl-pyrazine was prepared by first forming 5-methyl-3-oximino-2-hexanone by reacting 5-methyl-2-hexanone with nitrosyl chloride according to the method of BOUVEAULT (loc.cit.). The autocondensation of two moles of the imino-ketone in the presence of zinc and acetic acid [according to the method described in Chimia 11, 310 (1957)] yielded 2,5-dimethyl-3,6-diisobutyl-pyrazine which had a b.p. of 69°-70° C./0.01 mm. Hg.

(5) g. 2,5-Dimethyl-3,6-diamyl-pyrazine was prepared by first forming 3-oximino-2-octanone by reacting 2-octanone with nitrosyl chloride according to the method of BOUVEAULT (loc.cit.). The autocondensation of two moles of the imino-ketone in the presence of zinc and acetic acid [according to the method described in Chimia. 11, 310 (1957)] yielded 2,5-dimethyl-3,6-diamyl-pyrazine which had a b.p. of 78° C./0.03 mm. Hg.

(5) h. 2,5-Dimethyl-3,6-dihexyl-pyrazine was prepared by first forming 3-oximino-2-nonanone by reacting 2-nonanone with nitrosyl chloride according to the method of BOUVEAULT (loc.cit.). The autocondensation of two moles of the imino-ketone in the presence of zinc and acetic acid [according to the method described in Chimia 11, 310 (1957)] yielded 2,5-dimethyl-3,6-dihexyl-pyrazine which had a b.p. of 112°-120° C./0.01 mm. Hg.

(5) i. 2,3,5-Trimethyl-6-hexyl-pyrazine was prepared by introducing a hexyl group into the 6-position of 2,3,5-trimethylpyrazine by the method of Klein et al. (loc.cit.). The product had a b.p. of 89°-91° C./0.2 mm. Hg.

(5) j. 2,5-Dimethyl-3,6-diethyl-pyrazine is prepared by alkylation of 2,5-dimethyl-3-ethyl-pyrazine according to the alkyl-lithium method described by Klein et al. [J.A.C.S. 73, 2949 (1951)]. It has a b.p. of 83°-85° C./8 mm. Hg.

(6) a. 2-Ethyl-5-methyl-pyrazine was prepared by alkylation of 2,5-dimethyl-pyrazine following the procedure of Levine and Behun described in J.Org.Chem. 26, 3379 (1961). It has a boiling point of 60° C./11 mm. Hg.

(6) b. 2-Isopropyl-5-methyl-pyrazine was produced in the preparation of compound (6) a. as a by-product and was separated from the reaction mixture by gas chromatography. Identification was confirmed by mass spectrometry.

(6) c. 2,5-Diethyl-pyrazine was obtained by subjecting compound (6) a. to a second alkylation by the procedure given for compound (6) a. above. It boils at 64° C. at 12 mm. Hg.

(6) d. 2-Methyl-5-vinyl-pyrazine was prepared by the method of Levine et al. described at J.Org.Chem. 27, 1363 (1962), starting from 2,5-dimethyl-pyrazine. It has a boiling point of 65°-66° C./12 mm. Hg.

VIII. — ALIPHATIC AND AROMATIC ALCOHOLS

This group comprises compounds having the general formula:

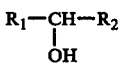

wherein
(1) $R_1$ is hydrogen or an alkyl group, e.g. methyl, ethyl, propyl; and $R_2$ is an alkyl group having at least 4 carbon atoms, e.g. from 4 to 9 carbon atoms; or
(2) $R_1$ is hydrogen or an alkyl group, e.g. comprising from 1 to 6 carbon atoms; and $R_2$ is an aryl group, e.g. phenyl; an aralkyl group, e.g. benzyl, phenylethyl; phenylpropyl; or an aralkenyl group, e.g. styryl, cinnamyl.

Compounds representative of this group include for instance:

| | | |
|---|---|---|
| (1) a. | n-amylalcohol | c.a. |
| b. | isoamylalcohol | c.a. |
| c. | n-hexanol | c.a. |
| d. | n-heptanol | c.a. |
| e. | n-octanol | c.a. |
| f. | n-nonanol | c.a. |
| g. | n-decanol | c.a. |
| h. | 2-heptanol | c.a. |
| i. | 3-octanol | o.a. |
| (2) a. | phenylethan-1-al | c.a. |
| b. | phenylpropan-1-ol | c.a. |
| c. | cinnamyl alcohol | c.a. |
| d. | phenyl methyl carbinol | c.a. |
| e. | benzyl methyl carbinol | c.a. |
| f. | benzyl ethyl carbinol | c.a. |
| g. | benzyl butyl carbinol | n.c. |
| h. | benzyl amyl carbinol | n.c. |
| i. | benzyl isoamyl carbinol | n.c. |
| j. | benzyl hexyl carbinol | n.c. |

The new compounds of this Group VIII can be prepared as follows:

(2) g. Benzyl butyl carbinol. To a solution of 1.05 mole of butyl-magnesium bromide in 400 ml. of ether there is added a solution of 1 mole (120 g.) of phenylacetaldehyde in 300 ml. of ether at −8° to −12° C. within 3 to 4 hours. The reaction mixture is heated to about 20°

C. and worked up by conventional methods. Distillation of the crude reaction product yields 99 g. of benzyl butyl carbinol of b.p. 88°–91° C./0.06 Torr; $d_4^{20} = 0.9485$; $n_D^{20} = 1.5059$.

The same method is used for preparing:
(2) h. Benzyl amyl carbinol, b.p. 81° C./0.01 Torr.
(2) i. Benzyl isoamyl carbinol, b.p. 142°–143° C./13 Torr; $d_4^{20} = 0.9377$; $n_D^{20} = 1.5009$.
(2) j. Benzyl hexyl carbinol, b.p. 95° C./0.01 Torr; $d_4^{20} = 0.9339$; $n_D^{20} = 1.4997$.

Organoleptic evaluation data are listed in TABLE VIII below.

IX. — FURAN ETHERS

The compounds of this group have the general formula:

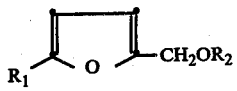

(1)

wherein $R_1$ and $R_2$ are hydrogen; alkyl, e.g. methyl, ethyl; aryl, e.g. phenyl, alkylphenyl; furfuryl, or alkylfurfuryl groups.

Compounds representative of this group include the following:

| | |
|---|---|
| (1) a. furfuryl methyl ether | Ber. 56, 1004 (1923) |
| b. furfuryl ethyl ether | Ber. 56, 1004 (1923) |
| c. furfuryl phenyl ether | Bull. 1938, 1151 |
| d. 5-methyl-furfuryl furfuryl ether | n.c. |
| e. difurfuryl ether | Am.Soc. 49, 1066 (1927) |

(1) d. 5-Methyl-furfuryl furfuryl ether was prepared by the procedure described by J. E. Zanetti in J.Am.Chem.Soc. 49, 1066 (1927) for the difurfuryl ether, starting with 5-methylfurfuryl bromide (Compt.Rend. 222, 1441 (1946)) instead of furfuryl bromide of Zanetti. The product was isolated by ether extraction of the crude mixture after having diluted with water. For purification the ether extract was distilled twice - b.p. 68°–70° C. at 0.01 mm./Hg vacuum. The product was a viscous colourless liquid, darkening rapidly on contact with air.

Organoleptic evaluations are tabulated in TABLE IX.

X — THIOPHENE ETHERS

This group of compounds are described by the structural formula:

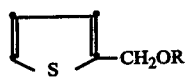

(1)

wherein R is an alkyl group, phenyl, alkylphenyl, furfuryl, alkylfurfuryl, or thenyl group, and includes for example:

| | |
|---|---|
| (1) a. thenyl methyl ether | J.A.C.S. 49, 1066 (1927) |
| | J.A.C.S. 50, 1960 (1928) |
| b. dithenyl ether | n.c. |
| c. furfuryl thenyl ether | n.c. |

The new compounds of this group were prepared as follows:

(1) b. Dithenyl ether. To a suspension of 1.32 g. (0.01 mole) of chloromethylthiophene [obtained by the method of F. F. BLICKE, J.A.C.S. 64, 477 (1942)] and 1.2 g. (0.02 mole) of powdered potassium hydroxide in 10 ml. of ether there is added a solution of 3.5 g. (0.03 mole) of thenyl alcohol in 10 ml. of ether. The reaction mixture is stirred for 1 hour at room temperature, then refluxed for 30 minutes and finally allowed to stand over night. After filtration the ethereal solution is concentrated and the residue fractionally distilled. There is obtained 0.22 g. (10%) of dithenyl ether having a b.p. of 99° C./0.01 mm. Hg. and a m.p. of 36.5°.

(1) c. Furfuryl thenyl ether is obtained by the same method as used for preparing compound (1) b., but using furfuryl alcohol instead of thenyl alcohol. The product thus obtained had a b.p. of 50° C./0.01 mm. Hg.

Organoleptic evaluation data on representatives of this group of compounds are set out in TABLE X below.

XI — THIAZOLE ALCOHOLS

Compounds of this group have the following structural formula:

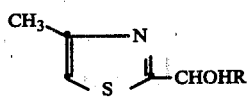

(1)

wherein R is an alkyl group, e.g. containing from 1 to 4 carbon atoms, or an alkenyl group, e.g. vinyl.

Representative compounds include the following:

| | |
|---|---|
| (1) a. methyl (4-methyl-thiazolyl-2) carbinol | n.c. |
| b. ethyl (4-methyl-thiazolyl-2) carbinol | n.c. |
| c. vinyl (4-methyl-thiazolyl-2) carbinol | n.c. |
| d. isobutyl (4-methyl-thiazolyl-2) carbinol | n.c. |

The new compounds of this Group X can be prepared as follows:

(1) a. Methyl (4-methyl-thiazolyl-2) carbinol was prepared by starting from 4-methyl-thiazole and substituting the hydrogen atom in the 2-position by lithium by reaction with butyllithium. The resulting metal-organic compound was reacted with acetaldehyde [cf. J.A.C.S. 74, 6260 (1952)]. The resulting product has a b.p. of 102°–103° C./9 mm. Hg.

(1) b. Ethyl (4-methyl-thiazolyl-2) carbinol was prepared by starting from 4-methyl-thiazole and substituting the hydrogen atom in the 2-position by lithium by reaction with butyllithium. The resulting metal-organic compound was reacted with propionaldehyde [cf. J.A.C.S. 74, 6260 (1952)]. The resulting product had a b.p. of 110°–115° C./9 mm. Hg. and a m.p. of 67°–72° C.

(1) c. Vinyl (4-methyl-thiazolyl-2) carbinol was prepared by starting from 4-methyl-thiazole and substituting the hydrogen atom in the 2-position by lithium by reaction with butyllithium. The resulting metal-organic compound was reacted with acrolein [cf. J.A.C.S. 74, 6260 (1952)]. The resulting product had a b.p. of 66° C./0.005 mm.Hg.

(1) d. Isobutyl (4-methyl-2-thiazolyl) carbinol was prepared by starting from 4-methyl-thiazole and substituting the hydrogen atom in the 2-position by lithium by reaction with butyllithium. The resulting metal-organic compound was reacted with isovaleraldehyde [cf. J.A.C.S. 74, 6260 (1952)]. The resulting product had a b.p. of 94° C./0.1 mm. Hg.

Organoleptic evaluations are set out in TABLE XI below.

XII — PYRIDINE ETHERS AND ALCOHOLS

Compounds of this group are found to have the following general formula:

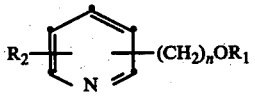
(1)

wherein $R_1$ is hydrogen or an alkoxy group, $R_2$ is hydrogen or an alkyl group, and $n$ is 0, 1 or 2. Examples of this group include:

| (1) | | |
|---|---|---|
| a. | 2-methoxy-pyridine | c.a. |
| b. | 2-butoxy-pyridine | n.c. |
| c. | 2-methoxymethyl-pyridine | c.a. |
| d. | 2-methoxymethyl-6-methyl-pyridine | c.a. |
| e. | 2-hydroxymethyl-pyridine | c.a. |
| f. | 3-hydroxymethyl-pyridine | c.a. |
| g. | 4-hydroxymethyl-pyridine | c.a. |
| h. | 2-hydroxymethyl-6-methyl-pyridine | c.a. |
| i. | 2-(2-hydroxyethyl)-pyridine | c.a. |
| j. | 2-(2-ethoxyethyl)-pyridine | c.a. |

(1) b. 2-Butoxy-pyridine was prepared according to the method described in J.A.C.S. 69, 1803 (1947) by condensing 0.17 mole of 2-bromo-pyridine with 0.195 mole of sodium butoxide. By distillation of the reaction product there were obtained 15 g. of 2-butoxy-pyridine distilling at 78° C./10 mm.Hg. $n_D^{23} = 1.4880$; $d_4^{23,4} = 0.9723$.

Organoleptic evaluations are set out in TABLE XII below.

XIII — Pyrazine Ethers and Alcohols

Compounds of this group are represented by the general formula:

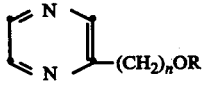
(1)

wherein R represents hydrogen or an alkyl group and $n$ is 0, 1 or 2.

Examples of compounds covered by this formula are:

| (1) | | |
|---|---|---|
| a. | 2-hydroxymethyl-pyrazine | J.Org.Chem. 28, 1898 (1963) |
| b. | 2-methoxymethyl-pyrazine | n.c. |
| c. | 2-ethoxymethyl-pyrazine | n.c. |

Compounds (1) b. and (1) c. were prepared by reacting 2-chloromethyl-pyrazine with the corresponding sodium alkoxide according to the same method as used for the preparation of sulfides [cf. HOUBEN-WEYL, 4th edition, vol. 9, 97 (1955)]. The products thus obtained had the following boiling points:
compound (1) b.: 51° C./8 mm. Hg.;
compound (1) c.: 75° C./8 mm. Hg.

Organoleptic evaluations are set out in TABLE XIII below.

XIV — Benzofuran Carbonyl Compounds

This group of compounds has the following general formula:

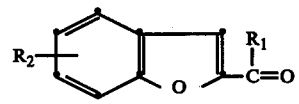
(1)

wherein $R_1$ and $R_2$ may be hydrogen or alkyl.

Examples of compounds included in this definition are:

| (1) | | |
|---|---|---|
| a. | benzofuran-2-aldehyde | Bull. 1962, 1875 |
| b. | 2-acetyl-benzofuran | J.A.C.S.73, 754 (1951) |
| c. | 7-methyl-benzofuran-2-aldehyde | n.c. |

(1) c. 7-Methyl-benzofuran-2-aldehyde was prepared by formylating 7-methyl-benzofuran according to the same method as used for the preparation of benzofuran-2-aldehyde. The product thus obtained has the following ion peaks in its mass spectrum: 160 (100%), 159 (62%) and 131 (33%).

Organoleptic evaluations are set out in TABLE XIV below.

XV — THIOPHENE ALDEHYDES

Compounds of this group have the general formulae:

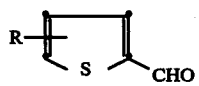
(1)

wherein R is hydrogen, or an alkyl or thenyl group; and

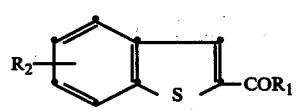
(2)

wherein $R_1$ and $R_2$ represent hydrogen or alkyl.

Compounds in this group include for instance:

| (1) | | |
|---|---|---|
| a. | Thiophene-2-aldehyde | c.a. |
| b. | 5-methyl-thiophene-2-aldehyde | Org.Syn. 36, 74 (1956) |
| c. | 3-methyl-thiophene-2-aldehyde | *b.p. 88–89° C./10 mm.Hg. |
| d. | 5-propyl-thiophene-2-aldehyde | *b.p. 64–65° C./0.002 mm.Mg. |
| e. | 5-thenyl-thiophene-2-aldehyde | *m.p. 31–32° c. |

*prepared according to the same method as used for compound (1) b.

| (2) | | |
|---|---|---|
| a. | benzothiophene-2-aldehyde | J.A.C.S.74, 2935 (1952) |
| b. | 2-acetyl-benzothiophene | Compt.Rend.234, 736 (1952) |

Organoleptic evaluations are set out in TABLE XV below.

XVI — PYRROLE ALDEHYDES

Compounds of this group have the structural formula

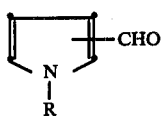

(1)

wherein R is an alkyl, furfuryl or thenyl group.
Representative compounds include, for example:

| | | |
|---|---|---|
| (1) a. | 1-ethyl-pyrrole-2-aldehyde | n.c. |
| b. | 1 butyl-pyrrole-2-aldehyde | Helv. 13, 349 (1930) |
| c. | 1-butyl-pyrrole-3-aldehyde | n.c. |
| d. | 1-amyl-pyrrole-2-aldehyde | n.c. |
| e. | 1-amyl-pyrrole-3-aldehyde | n.c. |
| f. | 1-α-methylbutyl-pyrrole-2-aldehyde | n.c. |
| g. | 1-α-methylbutyl-pyrrole-3-aldehyde | n.c. |
| h. | 1-furfuryl-pyrrole-2-aldehyde | Helv. 13, 349 (1930) |
| i. | 1-furfuryl-pyrrole-3-aldehyde | n.c. |
| j. | 1-thenyl-pyrrole-2-aldehyde | n.c. |
| k. | 1-isoamyl-pyrrole-2-aldehyde | Helv. 13, 349 (1930) |

The new compounds of this group XVI can be prepared as follows:

(1) a. 1-Ethyl-pyrrole-2-aldehyde was prepared from 1-ethyl-pyrrole [obtained by the method described in Helv. 10, 387 (1927] by introducing a formaldehyde group following the technique described in Org.Synth. 36, 74 (1956). The product boiled at 73°–75° C./7 mm. Hg.

(1) c. 1-Butyl-pyrrole-3-aldehyde was prepared by the same method as used for compound (1) a. It has a b.p. of 148°–150° C./11 mm. Hg.

(1) d. 1-Amyl-pyrrole-2-aldehyde was prepared by the same method as used for compound (1) a. It has a b.p. of 111°–112° C./11 mm. Hg.

(1) e. 1-Amyl-pyrrole-3-aldehyde was prepared by the same method as used for compound (1) a. It has a b.p. of 155°–160° C./11 mm.Hg.

(1) f. 1-α-Methylbutyl-pyrrole-2-aldehyde was prepared by the same method as used for compound (1) a. It has a b.p. of 103°–105° C./11 mm. Hg.

(1) g. 1-α-Methylbutyl-pyrrole-3-aldehyde was prepared by the same method as used for compound (1) a. It has a b.p. of 150° C./11 mm. Hg.

(1) h. 1-Furfuryl-pyrrole-2-aldehyde was prepared starting with 1-furfuryl-pyrrole described by Reichstein in Helv. 15, 1450 (1932) as well as Gianturco et al. In Tetrahedron 20, 1763 (1964). The aldehyde group was introduced by the Vilameyer reaction (e.g. by the method described in Bull. 1962, 1989). A small amount of the corresponding 3-aldehyde is obtained as a by-product and can be separated by fractional distillation. The 2-aldehyde boils at 139°–140° C./12 mm. Hg. and is a viscous colorless oil. The 3-aldehyde has a b.p. of 190° C./12 mm. Hg.

(1) j. 1-Thenyl-pyrrole-2-aldehyde was prepared by the same method as used for compound (1) h. It has a b.p. of 98° C./0.005 mm. Hg.

The organoleptic evaluations are shown in TABLE XVI below.

XVII — PYRAZINE CARBONYL COMPOUNDS

Compounds of this group have the general formula:

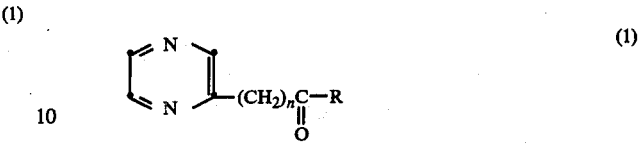

(1)

wherein R is hydrogen or an alkyl group and $n$ is 0 or 1.
Examples of this group include:

| | | |
|---|---|---|
| (1) a. | 2-formyl-pyrazine | C.A. 58, 10180b (1963) |
| b. | 2-acetyl-pyrazine | J.A.C.S. 74, 3621 (1952) |
| c. | 1-acetonyl-pyrazine | J.Org.Chem.23, 406 (1958) |

Organoleptic evaluations are tabulated in TABLE XVII below.

XVIII — ALIPHATIC AND AROMATIC KETONES

The compounds of this group are defined by the following general formula:

$$R_1-CO-R_2 \qquad (1)$$

wherein $R_1$ is an alkyl group having from 1 to 3 carbon atoms and $R_2$ is an alkyl group having from 3 to 11 carbon atoms, or a phenyl or benzyl group.

Examples of compounds corresponding to this definition are as follows:

| | | |
|---|---|---|
| (1) a. | methyl amyl ketone | c.a. |
| b. | methyl hexyl ketone | c.a. |
| c. | methyl heptyl ketone | c.a. |
| d. | methyl octyl ketone | c.a. |
| e. | methyl nonyl ketone | c.a. |
| f. | methyl decyl ketone | c.a. |
| g. | methyl undecyl ketone | c.a. |
| h. | ethyl butyl ketone | c.a. |
| i. | ethyl amyl ketone | c.a. |
| j. | dipropyl ketone | c.a. |
| k. | propyl isopropyl ketone | J.A.C.S. 63, 3163 (1941) |
| l. | di-isopropyl ketone | J.A.C.S. 59, 1826 (1937) |
| m. | acetophenone | c.a. |
| n. | propiophenone | c.a. |
| o. | isopropyl phenyl ketone | c.a. |
| p. | methyl benzyl ketone | c.a. |
| q. | ethyl benzyl ketone | c.a. |

Organoleptic evaluations are tabulated in TABLE XVIII below.

XIX — FURAN KETONES

This family of compounds have the following general formula:

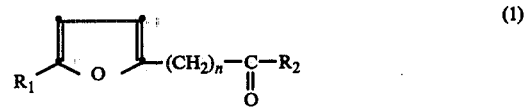

(1)

wherein $n$ is 0, 1 or 2 and wherein $R_1$ is hydrogen or methyl, and $R_2$ is alkyl.

Representative examples of compounds in this group include:

| | | |
|---|---|---|
| (1) a. | 2-acetyl-furan | c.a. |
| b. | 2-propionyl-furan | J.A.C.S. 72, 3695 (1950) |

-continued

| | | |
|---|---|---|
| c. | 2-butyryl-furan | J.A.C.S. 72, 3695 (1950) |
| d. | 2-valeryl-furan | J.A.C.S. 72, 3695 (1950) |
| e. | 5-methyl-2-acetyl-furan | J.A.C.S. 72, 3695 (1950) |
| f. | 5-methyl-2-propionyl-furan | J.A.C.S. 72, 3695 (1950) |
| g. | furfuryl methyl ketone | Ber. 76, 192 (1943) |
| h. | furfuryl ethyl ketone | J.Org.Chem. 15, 8 (1950) |
| i. | (5-methyl-furfuryl) methyl ketone | n.c. |
| j. | (5-methyl-furfuryl) ethyl ketone | n.c. |
| k. | 4-furyl-2-butanone | J.A.C.S. 72, 3695 (1950) |
| l. | 4-(5-methylfuryl)-2-butanone | Ber. 76, 192 (1943) |
| m. | 1-(5-methylfuryl)-3-pentanone | n.c. |

The new compounds of this group can be prepared as follows:

(1) i. (5-Methyl-furfuryl) methyl ketone was prepared according to the procedure described by Haas et al. in J.Org.Chem. 15, 8 (1950) by condensing 5-methyl-furfuryl-aldehyde with nitroethane. The product has a b.p. of 75° C./10 mm Hg.

(1) j. (5-Methyl-furfuryl) ethyl ketone was prepared by the same method as used for compound (1) i., except that 1-nitropropane was used instead of nitroethane. The product has a b.p. of 97°–100° C./15 mm. Hg.

(1) m. 1-(5-Methylfuryl)-3-pentanone was prepared by the method described in Ber. 76, 192 (1943). It has a b.p. of 101°–102° C./11 mm. Hg.

Organoleptic evaluation data are set out in TABLE XIX below.

XX — THIOPHENE KETONES

Compounds of this group which have been found to have utility in the concept of the instant invention have the following general formulae:

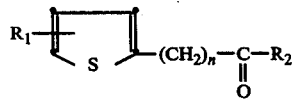
(1)

wherein $n$ is 0 or 1, $R_1$ is hydrogen or alkyl and $R_2$ is alkyl; and

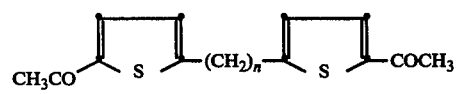
(2)

wherein $n$ is 0 or 1.

Representative compounds include:

| | | |
|---|---|---|
| (1) a. | 2-acetyl-thiophene | J.A.C.S. 72, 3695 (1950) |
| b. | 3-methyl-2-acetyl-thiophene | J.A.C.S. 72, 3695 (1950) |
| c. | 4-methyl-2-acetyl-thiophene | J.A.C.S. 72, 3695 (1950) |
| d. | 3-methyl-2-propionyl-thiophene | J.A.C.S. 72, 3695 (1950) |
| e. | 5-methyl-2-propionyl-thiophene | J.A.C.S. 72, 3695 (1950) |
| f. | 2-butyryl-thiophene | J.A.C.S. 72, 3695 (1950) |
| g. | 5-methyl-2-acetyl-thiophene | J.A.C.S. 72, 3695 (1950) |
| h. | 2-propionyl-thiophene | J.A.C.S. 72, 3695 (1950) |
| i. | 2-acetylmethyl-thiophene | C.A. 51, 10509c (1957) |
| (2) a. | 5,5'-diacetyl-dithienyl-2,2'-methane | J.A.C.S. 73, 1270 (1951) |
| b. | 5,5'-diacetyl-dithienyl-2,2' | J.A.C.S. 78, 1958 (1956) |

Organoleptic evaluation data are set out in TABLE XX below.

XXI — PYRROLE KETONES

Compounds of this group have the general formulae:

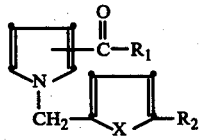
(1)

wherein X is oxygen or sulfur, $R_1$ is an alkyl group, and $R_2$ is hydrogen or an alkyl group;

(2)

wherein R is an alkyl group;

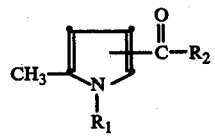
(3)

wherein $R_1$ is hydrogen or an alkyl group and $R_2$ is an alkyl group;

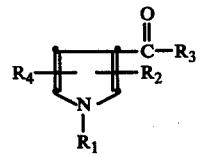
(4)

wherein $R_1$, $R_2$ and $R_4$ represent hydrogen or alkyl groups and $R_3$ is an alkyl group.

Compounds which are representative of this group include:

| | | |
|---|---|---|
| (1) a. | 1-furfuryl-2-acetyl-pyrrole | n.c. |
| b. | 1-thenyl-2-acetyl-pyrrole | J.A.C.S. 85, 2859(1963) |
| c. | 1-thenyl-3-acetyl-pyrrole | J.A.C.S. 85, 2859 (1963) |
| (2) a. | 1-acetyl-pyrrole | Chem. & Ind. 1965, 1426 |
| b. | 1-propionyl-pyrrole | Ber. 89, 1938 (1956) |
| (3) a. | 2-methyl-5-acetyl-pyrrole | c.a. |
| b. | 1,2-dimethyl-5-acetyl-pyrrole | n.c. |
| (4) a. | 2,5-dimethyl-3-acetyl-pyrrole | Beilstein XXI, 277 (1935) |
| b. | 1-methyl-3-acetyl-pyrrole | n.c. |

The new compounds included in this group can be prepared as follows:

(1) a. 1-Furfuryl-2-acetyl-pyrrole was prepared starting from 1-furfuryl-pyrrole described by Reichstein in Helv. 15, 1450 (1932) as well as Gianturco et al. in Tetrahedron 20, 1763 (1964). Acetylation by reaction of the Grignard intermediate with acetyl chloride [cf. Chem. Ber. 47, 1416 (1914)] led to the desired ketone. (A small amount of the 3-isomer was also obtained, separable by fractional distillation). The product boils at 100°-102° C./0.03 mm Hg. and crystallizes on standing. Recrystallization from a mixture of methylene dichloride and petroleum ether gave a white crystalline product with a m.p. of 42°-43° C.

(3) b. 1,2-Dimethyl-5-acetyl-pyrrole was obtained by acetylating 1,2-dimethylpyrrole according to the method described in Ber. 47, 1416 (1914) [cf. also J.A.C.S. 85, 2859 (1963)]. The product has a b.p. of 102°-106° C./10 mm. Hg.

(4) b. 1-Methyl-3-acetyl-pyrrole was obtained as a by-product in the synthesis of 1-methyl-2-acetyl-pyrrole according to the method described in Ber. 47, 1416 (1914). The product has a b.p. of 130°-132° C./12 mm. Hg.

Evaluation data are set out in TABLE XXI below.

XXII — THIAZOLE CARBONYL COMPOUNDS

Compounds of this group have the following general formula:

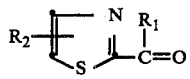

(1)

wherein $R_1$ and $R_2$ are hydrogen or alkyl groups.

Representative compounds of this group are:

| (1) a. 4-methyl-2-acetyl-thiazole | Bull. 20, 702 (1953) |
|---|---|
| b. 4-methyl-2-propionyl-thiazole | n.c. |
| c. 5-methyl-2-acetyl-thiazole | Bull. 20, 702 (1953) |
| d. 4-methyl-2-butyryl-thiazole | n.c. |
| e. 4-methyl-2-formyl-thiazole | n.c. |

The new compounds included in this group can be prepared as follows:

(1) b. 4-Methyl-2-propionyl-thiazole was prepared according to the method described in Bull. 20, 702 (1953) by reacting 4-methyl-thiazole with ethyl-magnesium bromide and acylating the obtained Grignard intermediate with propionyl chloride. The product has a b.p. of 83°-88° C./9 mm. Hg.

(1) d. 4-Methyl-2-butyryl-thiazole was prepared by the same method as compound (1) b, but using butyric anhydride as the acylating agent. The product has a b.p. of 110°-115° C./8 mm. Hg.

(1) e. 4-Methyl-2-formyl-thiazole was prepared by oxidizing 2-hydroxymethyl-4-methyl-thiazole with chromic acid in a sulfuric acid medium according to the method described in J.A.C.S. 53, 1470 (1931). The product was identified by mass spectrometry (peaks M/e and relative intensity): 71 (100%), 127 (97%) and 72 (48%).

Organoleptic evaluation data are set out in TABLE XXII below.

XXIII — PYRIDINE CARBONYL COMPOUNDS

Compounds of this group have the general formula:

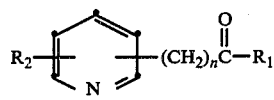

(1)

wherein $R_1$ represents hydrogen, an alkyl group or a phenyl group, $R_2$ represents hydrogen, an alkyl group or an acyl group and $n$ is 0, 1 or 2.

Representative compounds include:

| | |
|---|---|
| (1) a. 2-acetyl-pyridine | c.a. |
| b. 6-methyl-2-acetyl-pyridine | c.a. |
| c. 3-acetyl-pyridine | c.a. |
| d. 4-acetyl-pyridine | c.a. |
| e. pyridine-2-aldehyde | c.a. |
| f. pyridine-3-aldehyde | c.a. |
| (1) g. pyridine-4-aldehyde | c.a. |
| h. 6-methyl-pyridine-2-aldehyde | c.a. |
| i. 2-benzoyl-pyridine | c.a. |
| j. 3-benzoyl-pyridine | c.a. |
| k. 4-benzoyl-pyridine | c.a. |
| l. 2,6-diacetyl-pyridine | c.a. |
| m. 4-(γ-pyridyl)-butan-2-one | n.c. |

The new compound, 4-γ-pyridyl)-butan-2-one, was prepared as follows:

8 ml. of 2-n NaOH solution were added to a mixture of 10.8 g (0.1 mole) of pyridine-4-aldehyde, 100 ml. of water and 10 ml. of acetone at 12°-15° C. After a reaction time of 3 minutes the reaction mixture was neutralized with 10% aqueous acetic acid, saturated with NaCl and extracted with ether. After removal of the ether the residue was distilled. There were obtained 8.4 g. of 4-(γ-pyridyl)-3-buten-2-one as a yellow oil of b.p. 135°-138° C./0.07 Torr 5.24 g. of this product were dissolved in 30 ml. of ethanol and hydrogenated in the presence of 4 g. of Ni-catalyst. Distillation of the reaction product yielded 4-(γ-pyridyl)-butan-2-one of b.p. 83°-85° C./0.05 Torr; $n_4^{27} = 1.047$; $n_D^{27} = 1.516$.

Organoleptic evaluation data are set out in TABLE XXIII below.

XXIV — Alpha-Diketones

Compounds of this group which have been found to have utility in the concept of this invention are of the formulae:

$$CH_3COCOR \quad (1)$$

$$C_2H_5COCOR \quad (2)$$

wherein R is an alkyl group or a phenyl group. Compounds representative of this group include:

| (1) a. acetylbutyryl | J.Chem.Soc. 1946, 56 |
|---|---|
| b. acetylisobutyryl | Ber. 22, 2121 (1889) |
| c. acetylisovalerianyl | Ber. 22, 2122 (1889) |
| d. acetylcaproyl | J.pr.Ch.[2] 58, 402 (1898) $n_D^{20} = 1.4214$; $d_4^{20} = 0.9183$ |
| e. acetylbenzoyl | c.a. (British Drug House) |
| f. 5-methyl-heptanedione-2,3 | n.c. |
| g. 5-methyl-octanedione-2,3 | n.c. |
| h. acetylvalerianyl | n.c. |
| i. acetylheptanoyl | n.c. |
| (2) a. dipropionyl | Bull.[3], 31, 629,650 (1906) |
| b. heptane-3,4-dione | Bull.[3], 31, 1174 (1904) |
| c. 5-methyl-heptane-3,4-dione | n.c.; prepared by the method in Bull.[3], 31, 1174 (1904); b.p. 55° C./12 mm.Hg. |

The new compounds included in this group can be obtained as follows:

(1) f. 5-Methyl-heptan-2,3-dione. 0.33 Mole of acetoI, 0.33 mole of α-methylbutanal and 2.5 ml. of conc. HCl were heated in a flask equipped with a Raschig column (length 25 cm), and the volatile products were distilled over as the reaction proceeded. 15 ml. of distillate were collected and rejected. The flask was cooled, and 15 ml. of water were added to the distillation residue. The distillation was then continued at a bath temperature of 150°-180° C. After 15 ml. of distillate consisting of the reaction product and water had been collected, the flask was again cooled, and the addition of water followed by distillation were repeated several times until the reaction product was completely distilled. The combined distillates were extracted with ether, after washing the extract with aqueous sodium carbonate and water and evaporation of the solvent, the residue was distilled. There were obtained 3.9 g. of pure 5-methyl-heptan-2,3-dione distilling at 45°-47° C./8 Torr. $n_D^{23.5} = 1.4200$; $d_4^{23.5} = 0.9099$.

(1) g. 5-Methyl-octan-2,3-dione was prepared according to the same method as 5-methyl-heptan-2,3-dione, except that 0.5 mole of acetol, 0.55 mole of α-methyl-pentenal and 4.5 ml. of conc. HCl were used for the reaction. There were obtained 16 g. of pure 5-methyl-octan-2,3-dione distilling at 65°-66° C./11 Torr; $n_D^{22.5} = 1.4258$; $d_4^{22.5} = 0.9107$.

(1) h. Acetylvalerianyl was prepared according to the same method as compound (1) f. It has a b.p. of 71°-72° C./44 mm.Hg.

(1) i. Acetylheptanoyl was prepared by hydrolyzing 3-oximino-nonan-2-one according to the method of Bouveault et al. described in Bull.Soc.Chim. France [3] 31, 1145 (1904). 3-Oximino-nonan-2-one was obtained by nitrosation of nonan-2-one with ethyl nitrite according to the method described in Org.React. VII, Chap. 6 (1953). Acetylheptanoyl has a b.p. of 74° C./9 mm. Hg.

(2) c. 5-Methyl-heptan-3,4-dione was prepared according to the method described in Bull [3], 31, 1145 (1904). It has a b.p. of 55° C./12 mm. Hg.

The organoleptic evaluations are set out in TABLE XXIV below.

XXV — THIOPHENE ALPHA-DIKETONES

Compounds of this group have the following general formula:

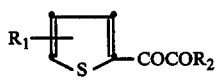

(1)

wherein $R_1$ is hydrogen or a methyl group and wherein $R_2$ is an alkyl group.

Representative compounds include:

| | |
|---|---|
| (1) a. 1-(thienyl-2)-propane-1,2-dione | n.c. |
| b. 1-(3-methyl-thienyl-2)-propane-1,2-dione | n.c. |
| c. 1-(5-methyl-thienyl-2)-propane-1,2-dione | n.c. |
| d. 1-(thienyl-2)-butan-1,2-dione | n.c. |

The new compounds included in this group can be obtained as follows:

(1) a. 1-(Thienyl-2)-propane-1,2 dione was prepared by acylating thiophene according to the method described in J.A.C.S. 72, 3695 (1950), subjecting the resulting 2-propionylthiophene to the action of nitrosyl chloride and hydrolyzing the reaction product in formic acid solution with nitrosyl sulfuric acid as described in Bull. [3] 31, 1163 (1904). The product formed bright yellow crystals and melted at 48°-50° C.

(1) b. 1-(3-methyl-thienyl-2)-propane-1,2 dione was prepared by acylating thiophene according to the method described in J.A.C.S. 72, 3695 (1950), subjecting the resulting 3-methyl-2-propionyl-thiophene to the action of nitrosyl chloride and hydrolizing the reaction product in formic acid solution with nitrosyl sulfuric acid as described in Bull. [3] 31, 1163 (1904). The product had a b.p. of 93° C./11 mm. Hg.

(1) c. 1-(5-Methyl-thienyl-2)-propane-1,2-dione was prepared by the same method as compound (1) a. It has a b.p. of 150°-160° C. (bath temp.)/11 mm. Hg.

(1) d. 1-(Thienyl-2)-butan-1,2-dione was prepared from 2-butyryl-thiophene via the oxime according to the method used in the furan series and described in Tetrahedron 20, 2959 (1964). The product has a b.p. of 120°-123° C. (bath temperature) 11 mm. Hg.

The organoleptic evaluations gave the results set out in TABLE XXV below.

XXVI — PYRROLE ALPHA-DIKETONES

This group of compounds has the general formula:

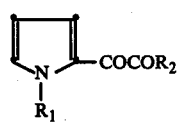

(1)

wherein $R_1$ is hydrogen or alkyl and $R_2$ is alkyl.

Representative compounds of this group include e.g.:

| | |
|---|---|
| (1) a. (pyrrolyl-2)-propan-1,2-dione | n.c. |
| b. (pyrrolyl-2)-butan-1,2-dione | n.c. |

The new compounds included in this group can be obtained as follows:

(1) a. (Pyrrolyl-2)-propan-1,2-dione was prepared according to the same method as used for compound (1) d. of Group XXV. It has a m.p. of 50°-51° C.

(1) b. (Pyrrolyl-2)-butan-1,2-dione was prepared by the same method as used for compound (1) d. of Group XXV. It has a m.p. of 37°-38° C.

Organoleptic evaluation data are set out in TABLE XXVI below.

XXVII — FURAN ESTERS

Compounds of this group have the general formulae:

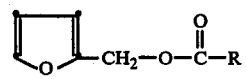

(1)

wherein R is an alkyl group comprising at least 2 carbon atoms; and

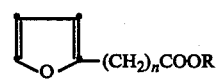

(2)

wherein R is an alkyl or alkenyl group.

Representative compounds of this group include:

| | |
|---|---|
| (1) a. furfuryl propionate | *"The Furans", page 226 |
| b. furfuryl butyrate | *"The Furans", page 226 |
| c. furfuryl isobutyrate | *"The Furans", page 226 |
| d. furfuryl isovalerate | n.c. |
| e. furfuryl crotonate | n.c. |
| f. furfuryl tiglate | *"The Furans", page 36 |
| g. furfuryl alphamethylbutyrate | n.c. |
| h. furfuryl β,β'-dimethylacrylate | n.c. |
| i. furfuryl valerate | n.c. |
| (2) a. ethyl furoate | *"The Furans", page 513 |
| b. propyl furoate | *"The Furans", page 513 |
| c. isopropyl furoate | *"The Furans", page 513 |
| d. butyl furoate | *"The Furans", page 513 |

-continued

| | |
|---|---|
| e. isobutyl furoate | *"The Furans", page 513 |
| f. isoamyl furoate | *"The Furans", page 513 |
| g. methyl 3-(α-furyl)-propionate | C.A. 32, 53977 (1938) |
| h. ethyl 3-(α-furyl)-propionate | c.a |

*"The Furans", Reinhold Publishing Company, New York (1953).

The new compounds included in this group can be obtained by reacting the corresponding acid chlorides with furfuryl alcohol, e.g. according to the method described in Houben-Weyl, 4th ed., Vol. 8, 543 (1952). There are thus obtained:

(1) d. Furfuryl isovalerate, b.p. 97°–98° C./11 mm. Hg.
(1) e. Furfuryl crotonate, b.p. 96°–98° C./11 mm. Hg.
(1) g. Furfuryl α-methylbutyrate, b.p. 96° C./11 mm. Hg.
(1) h. Furfuryl β,β'-dimethylacrylate, b.p. 113°–115° C./11 mm. Hg.
(1) i. Furfuryl valerate, b.p. 100°–104° C./11 mm. Hg.

In the organoleptic evaluation tests these compounds gave the results set out in TABLE XXVII below.

XXVIII — THIOPHENE ESTERS

Compounds of this group have the following general formulae:

$$\text{(thiophene)}-COOR \quad (1)$$

wherein R is alkyl or furfuryl; and $$\text{(thiophene)}-CH_2OOCR \quad (2)$$

wherein R is hydrogen or alkyl.

Representative compounds of this group include:

| | |
|---|---|
| (1) a. methyl thiophene-2-carboxylate | J.A.C.S. 77, 6709 (1955) |
| b. ethyl thiophene-2-carboxylate | J.A.C.S. 77, 6709 (1955) |
| c. propyl thiophene-2-carboxylate | J.A.C.S. 77, 6709 (1955) |
| d. butyl thiophene-2-carboxylate | J.A.C.S. 77, 6709 (1955) |
| e. isoamyl thiophene-2-carboxylate | n.c. |
| f. furfuryl thiophene-2-carboxylate | n.c. |
| (2) a. thenyl formate | n.c. |
| b. thenyl acetate | n.c. |

The new compounds included in sub-class (1) of this group can be obtained by reacting thionyl chloride with the corresponding alkoxides according to the method described in J.A.C.S. 77, 6709 (1955). There were thus obtained:

(1) e. Isoamyl thiophene-2-carboxylate, b.p. 79°–80° C./0.3 mm. Hg.
(1) f. Furfuryl thiophene-2-carboxylate, b.p. 109° C./0.07 mm. Hg.

The new compounds included in sub-class (2) of this group can be obtained by acylation of 2-thenyl alcohol which is prepared by reducing thiophene-2-aldehyde according to the method described in J.Org.Chem. 15, 790 (1950). Acylation with the mixed anhydride of formic and acetic acids according to the method described in J.A.C.S. 64, 1583 (1942) yields (2) a. Thenyl formate, b.p. 87°–88° C./15 mm. Hg.
Acylation with acetic anhydride yields (2) b. Thenyl acetate, b.p. 91° C./12 mm. Hg.

In the organoleptic evaluation test these compounds gave the results set out in TABLE XXVIII below.

XXIX — PYRIDINE ESTERS

Compounds of this group are of the general formula $$\text{(pyridine)}-(CH_2)_n COOR \quad (1)$$

wherein R stands for lower alkyl and n is 0 or 1.
Representative compounds of this group include:

| | |
|---|---|
| (1) a. methyl (pyridyl-2)-acetate | c.a. |
| b. methyl (pyridyl-3)-acetate | c.a. |
| c. methyl (pyridyl-4)-acetate | c.a. |
| d. ethyl (pyridyl-2)-acetate | c.a. |
| e. ethyl (pyridyl-3)-acetate | c.a. |
| f. ethyl (pyridyl-4)-acetate | c.a. |

Organoleptic evaluation data are set out in TABLE XXIX below.

XXX — AROMATIC SULFUR COMPOUNDS

Compounds of this group are of the general formulae:

$$\text{(benzene with SH, } R_1, R_2 \text{)} \quad (1)$$

wherein $R_1$ stands for hydrogen, hydroxy, alkoxy or alkyl and $R_2$ represents hydrogen or alkyl;

$$\text{(benzene with }(CH_2)_n-S-R_3, R_1, R_2\text{)} \quad (2)$$

wherein $R_1$ stands for hydrogen, hydroxy, alkyl or alkoxy, $R_2$ may be hydrogen or alkyl, $R_3$ represents alkyl or benzyl and n is 0, 1 or 2; and $$\text{(benzene)}-S-S-R \quad (3)$$

wherein R stands for alkyl or phenyl.
Representative compounds include:

| | |
|---|---|
| (1) a. 2-methoxy benzenethiol | Ber.39, 1348 (1906) |
| b. benzenethiol | c.a. |
| c. 2-hydroxy-thiophenol | Beilstein 6, 793 |
| d. 2-methyl-benzenethiol | c.a. |
| e. 3-methyl-benzenethiol | c.a. |
| f. 4-methyl-benzenethiol | c.a. |
| g. 2,4-dimethyl-benzenethiol | Ber. 32, 1147 |
| h. 3,4-dimethyl-benzenethiol | J.Org.Chem. 26, 4047 (1961) |
| i. 2-ethyl-benzenethiol | Ber. 59, 349 |
| j. 2-ethoxy-benzenethiol | J.pr.Ch. 114, 231, 235 |
| k. 4-methoxy-benzenethiol | c.a. |
| (2) a. methyl phenyl sulfide | c.a. |

-continued

| | |
|---|---|
| b. dibenzyl sulfide | J.Chem.Soc. 1922, 1404 |
| (3) a. phenyl methyl disulfide | J.A.C.S. 85, 1618 (1963) |
| b. diphenyl disulfide | Ber. 56, 1929 (1923) |

Evaluation test data are set out in TABLE XXX below.

XXXI — FURAN SULFUR COMPOUNDS

Compounds of this group are included in the formulae:

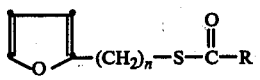  (1)

wherein R may be hydrogen, alkyl or alkenyl and $n$ stands for 1 or 2;

  (2)

wherein $R_1$ stands for hydrogen or alkyl, $R_2$ represents hydrogen, alkyl, furfuryl or alkyl-substituted phenyl, and $n$ stands for 0, 1 or 2, with the provision that, if $R_1$ is hydrogen and $n$ is 1, $R_2$ is neither methyl nor furfuryl;

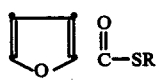  (3)

wherein R is alkyl or furfuryl;

  (4)

wherein $R_1$ represents hydrogen or alkyl and $R_2$ stands for alkyl or furfuryl; and

  (5)

wherein R represents an alkyl or an acyl group.
Representative compounds in this group include:

| | |
|---|---|
| (1) a. furfurylthiol acetate | n.c. |
| b. furfurylthiol propionate | n.c. |
| c. furfurylthiol butyrate | n.c. |
| d. furfurylthiol furoate | n.c. |
| e. furfurylthiol β,β-dimethylacrylate | n.c. |
| f. furfurylthiol tiglate | n.c. |
| g. furfurylthiol formate | n.c. |
| h. 2-(furyl-2)-ethanthiol acetate | n.c. |
| (2) a. 5-methylfurfuryl methyl sulfide | n.c. |
| b. furfuryl propyl sulfide | n.c. |
| c. furfuryl isopropyl sulfide | n.c. |
| d. furfuryl 5-methylfuryl sulfide | n.c. |
| e. 5-methylfuryl methyl sulfide | n.c. |
| f. 2-(furyl-2)-ethanthiol | n.c. |
| (3) a. methylthiol furoate | n.c. |
| (4) a. difurfuryl disulfide | J.A.C.S. 52, 2141 (1930) |
| (5) a. (benzofuryl-2)-methyl methyl sulfide | n.c. |
| b. (benzofuryl-2)-methylthiol acetate | n.c. |

The new compounds included in this group XXXI can be obtained as follows:

(1) a. Furfurylthiol acetate was prepared by reacting acetic chloride or anhydride with furfurylmercaptan according to the method described in Houben-Weyl, 4th ed., vol. 9, 753 (1955). The product has a b.p. of 90°–92° C./12 mm. Hg.

According to the same method, but starting from the corresponding acid chloride or anhydride, the following products were obtained:

(1) b. Furfurylthiol propionate, b.p. 95°–97° C./10 mm.Hg.

(1) c. Furfurylthiol butyrate, b.p. 105.5°–106.5°/10 mm. Hg.

(1) d. Furfurylthiol furoate, b.p. 110° C./0.01 mm. Hg.

(1) e. Furfurylthiol β,β-dimethylacrylate, b.p. 85° C./0.015 mm. Hg.

(1) f. Furfurylthiol tiglate, b.p. 84.5°–87.5° C./0.03 mm. Hg.

(1) g. Furfurylthiol formate was prepared according to the method used for the synthesis of furfuryl formate and described in J.A.C.S. 64, 1583 (1942). The product had a b.p. of 77°–78° C./8 mm. Hg.

(1) h. 2-(Furyl-2)-ethanthiol acetate was prepared by reacting thioacetic acid with 2-vinyl-furane under the action of UV light and in the presence of benzoyl peroxide according to the method described in J.Org.Chem. 27, 2853 (1962). The thio-ester, after isolation by distillation had a b.p. of 100°–103° C./0.05 mm. Hg.

(2) a. 5-Methylfurfuryl methyl sulfide was prepared by reacting 5-methylfurfuryl-mercaptan with dimethyl sulfate in alkaline solution according to known methods. 5-Methylfurfurylmercaptan was obtained from the corresponding alcohol by the method described in Org.Syn. 35, 67 (1955). The product is a colorless liquid boiling at 71°–72° C./11 mm. Hg.

(2) b. Furfuryl propyl sulfide was prepared by reacting sodium furfurylmercaptide with n-propyl bromide according to the method described in Houben-Weyl, 4ht ed., vol. 9, 97 (1955). The product has a b.p. of 91° C./15 mm. Hg.

(2) c. Furfuryl isopropyl sulfide was prepared by the same method as used for compound (2) b., except that isopropyl bromide was used instead of n-propyl bromide. The product has a b.p. of 84° C./16 mm. Hg.

(2) d. Furfuryl 5-methylfuryl sulfide was prepared according to the method used for the synthesis of alkylthio-furans and described in C.A. 59, 8681d (1963). 2-Methylfuran was reacted with butyl-lithium and then with sulfur. The resulting thiol was further reacted (without prior isolation) with furfuryl chloride. The product was a slightly yellowish oil having a b.p. of 67° C./0.04–0.05 mm. Hg.

(2) e. Methyl 5-methylfuryl sulfide was prepared by the same method as used for compound (2) d. The product was a light yellow liquid having a b.p. of 80° C./45–50 mm. Hg.

(2) f. 2-(Furyl-2)-ethanethiol was prepared by saponifying 24 g. of 2-furylethanethiol acetate with alkali in aqueous-alcoholic medium. After refluxing for 90 minutes the reaction mixture was neutralized with acetic acid and then extracted with ether. Upon distillation there were obtained 14.4 g. of 2-(furyl-2)-ethanethiol having a b.p. of 61°–62° C./0.03 mm. Hg; $n_D^{22.3} = 1.5653$; $d_4^{23.2} = 1.153$ (3) a. Methylthiol fuorate was prepared by reacting furoyl chloride with methylmercaptan according to the method described in Houben-Weyl, 4th ed., vol. 9, 753 (1955). It has a b.p. of 92°-93° C./11 mm. Hg.

(5) a. Benzofurfuryl-2 methyl sulfide was prepared by reacting (benzofurfuryl-2)-mercaptan with dimethyl sulfate in alkaline solution. The sulfide thus obtained has a b.p. of 108°-109° C./0.4 mm. Hg.

The starting (benzofurfuryl-2)-mercaptan was obtained from the corresponding alcohol according to the method described in Org. Synth. 35, 67 (1955).

(5) b. (Benzofurfuryl-2)-thiol acetate was prepared by the same method as used for compound (1) a. (furfurylthiol acetate). The product has a b.p. of 120°-122° C./0.8 mm. Hg.

Evaluation test data are set out in TABLE XXXI below.

XXXII — THIOPHENE SULFUR COMPOUNDS

This group comprises compounds corresponding to the following general formulae:

(1)

wherein R represents hydrogen, alkyl, acetyl or thenyl, and $n$ is 1 or 2;
and

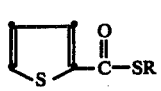
(2)

wherein R stands for alkyl or furfuryl.

Specific examples of compounds corresponding to these formulae include:

| (1) a. thenyl-mercaptan | Compt.rend. 229, 1343 (1949) |
|---|---|
| b. thenyl methyl sulfide | Compt.rend. 229, 1343 (1949) |
| c. thenylthiol acetate | n.c. |
| d. 2-(thienyl-2)-ethanethiol | n.c. |
| e. 2-(thienyl-2)-ethanethiol acetate | n.c. |
| f. dithenyl sulfide | n.c. |
| (2) a. thiothenoic acid S-methyl ester | n.c. |
| b. thiothenoic acid S-ethyl ester | n.c. |
| c. thiothenoic acid S-furfuryl ester | N.C. |

The new compounds of this group can be obtained as follows:

(1) c. Thenylthiol acetate was prepared by the same method as used for compound (1) a. (furfurylthiol acetate) of Group XXXI above. The product is a colorless liquid having a b.p. of 113°-114° C.

(1) d. 2-(Thienyl-2)-ethanethiol. 2-Vinyl-thiophene [obtained by the method described in Org. Synth. 38, 86 (1958)] was reacted with thioacetic acid according to the method described in J.Org.Chem. 27, 2853 (1962), and the resulting addition product was subjected to hydrolysis with an acid. The product has a b.p. of 55° C./0.1 mm. Hg.

(1) e. 2-(Thienyl-2)-ethanethiol acetate was obtained as the intermediate product obtained by reacting 2-vinyl-thiophene with thioacetic acid in the preparation of compound (1) d. above. The product has a b.p. of 90° C./0.07 mm. Hg.

(1) f. Dithenyl sulfide was prepared by the same method as used for compound (1) b. (dithenyl ether) of Group X above, except that thenylmercaptan was used instead of thenyl alcohol. The product has a b.p. of 118° C./0.04 mm. Hg.

Compounds (2) a, (2) b. and (2) c. were prepared by reacting thionyl chloride with the sodium salts of the corresponding mercaptans in alcoholic solution according to the method described in J.C.A.S. 77, 6709 (1955). After refluxing for 1 hour the reaction mixture was filtered and concentrated. The residue was purified by chromatography on a silica-gel column using a benzene-hexane mixture 8:2 as the eluant. The structure of the resulting products was identified by mass spectrometry:

(2) a. Thiothenoic acid S-methyl ester: Ion peaks with relative intensities: 111 (100%), 39 (22%) and 158 (12%).

(2) b. Thiothenoic acid S-ethyl ester: Ion peaks with relative intensities: 111 (100%), 39 (17%) and 172 (10%).

(2) c. Thiothenoic acid S-furfuryl ester: Ion peaks with relative intensities: 111 (100%), 81 (73.5%) and 39 (20%).

Organoleptic evaluation data are set out in TABLE XXXII below.

XXXIII — Pyridine Sulfur Compounds

The compounds included in this group have the general formula:

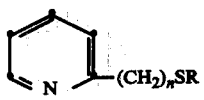
(1)

wherein R stands for hydrogen, alkyl, acyl or pyridyl, and $n$ is 0 or 1.

As examples there can be mentioned:

| (1) a. (pyridyl-2)-methanthiol | C.A. 55, 4542b (1961) |
|---|---|
| b. 2-mercapto-pyridine | c.a. |
| c. 2-methylthio-pyridine | n.c. |
| d. 2-ethylthio-pyridine | n.c. |
| e. (pyridyl-2)-thiol acetate | n.c. |
| f. di(pyridyl-2)-sulfide | J.Chem.Soc. 1942, 239 |
| g. 2-(pyridyl-2)-ethanethiol | J.Org.Chem. 26, 82 (1961) |
| h. 2-(pyridyl-2)-ethyl methyl sulfide | see below |
| i. 2-(pyridyl-2)-ethyl ethyl sulfide | n.c. |
| j. 2-(pyridyl-2)-ethanthiol acetate | see below |
| k. 2-(pyridyl-2)-ethyl furfuryl sulfide | n.c. |
| l. (pyridyl-2)-methyl methyl sulfide | Helv. 47, 1754 (1964) |
| m. (pyridyl-2)-methyl ethyl sulfide | n.c. |
| n. (pyridyl-2)-methanethiol acetate | n.c. |

The method used for preparing the known compound (1) h. [2-(pyridyl-2)-ethyl methyl sulfide] was as follows: 2-Vinylpyridine was reacted with methylmercaptan by the action of UV light in the presence of trace amounts of benzoyl peroxide and diphenyl sulfide. The product has a b.p. of 48° C./0.03 mm. Hg.

The same method was used for preparing the known compound (1) j., except that thioacetic acid was used instead of methylmercaptan. The product has a b.p. of 80° C./0.02 mm. Hg.

The new compounds included in this Group XXXIII can be obtained as follows:

(1) c. 2-Methylthio-pyridine was prepared according to the method described in Houben-Weyl, 4th, ed., vol. 9, 7 (1955) by alkylating 2-mercapto-pyridine with methyl halide. The resulting pyridinium salt was neutralized with NaOH and the base thus obtained extracted and distilled. The product had a b.p. of 67°–68° C./10 mm. Hg.

(1) d. 2-Ethylthio-pyridine was prepared by the same method as used for compound (1) c., except that ethyl halide was used instead of methyl halide. The product had a b.p. of 77°–77.5° C./8 mm. Hg.

(1) e. (Pyridyl-2)-thiol acetate was prepared by reacting acetic anhydride with 2-mercaptopyridine in alkaline medium according to the method described in Houben-Weyl, 4th ed., vol. 9, 753 (1955) and in J.A.C.S. 59, 1089 (1937). The product has a b.p. of 117°–118° C./9 mm. Hg.

(1) i. 2-(Pyridyl-2)-ethyl ethyl sulfide was prepared by the same method as used for compound (1) h., except that ethylmercaptan was used instead of methylmercaptan. The product has a b.p. of 62° C./0.005 mm. Hg.

(1) m. (Pyridyl-2)-methyl ethyl sulfide was prepared by the same method as used for compound (1) l. The product has a b.p. of 107°–110° C./10 mm. Hg.

(1) n. (Pyridyl-2)-methanethiol acetate was prepared by reacting acetyl chloride with 2-mercaptomethylpyridine in alkaline medium. The product has a b.p. of 102°–103° C./9 mm. Hg.

Evaluation test data are reported in TABLE XXXIII below.

XXXIV — Pyrrole Sulfur Compounds

These sulfur compounds correspond to the following general formula:

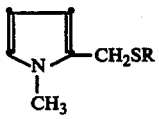

wherein R represents alkyl, furfuryl or acyl. As examples, there can be mentioned:

| (1) a. N-methyl-pyrryl-2 methyl sulfide | n.c. |
| b. N-methyl-pyrryl-2 ethyl sulfide | n.c. |
| c. N-methyl-pyrryl-2 furfuryl sulfide | n.c. |
| d. (N-methyl-pyrryl-2)-methylthiol acetate | n.c. |

The new compounds included in this Group XXXIV can be obtained as follows:

(1) a. N-Methyl-pyrryl-2 methyl sulfide was prepared by alkylating of N-methyl-(pyrryl-2)-methylmercaptan with methyl iodide according to the method described in Houben-Weyl, 4th ed., vol. 9, 97 (1955). The product has a b.p. of 90° C./10 mm. Hg.

(1) b. N-Methyl-pyrryl-2 ethyl sulfide was prepared by the same method as used for compound (1) a., except that ethyl bromide was used in place of methyl iodide. The product has a b.p. of 99° C./10 mm. Hg.

(1) c. N-Methyl-pyrryl-2-furfuryl sulfide was prepared by the same method as used for compound (1) a., except that furfuryl chloride was used in place of methyl iodide. The product has a b.p. of 94° C./0.01 mm. Hg.

(1) d. (N-Methyl-pyrryl-2)-methylthiol acetate was preparing by acylating (N-methy-pyrryl-2)-methylmercaptan according to the method described in Houben-Weyl, 4th ed., vol. 9, 753 (1958). The product has a b.p. of 69° C./0.05 mm. Hg.

Evaluation test data are set out in TABLE XXXIV below.

XXXV — Pyrazine Sulfur Compounds

The compounds of this group can be represented by the following general formulae:

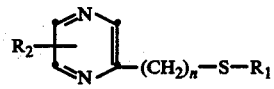

wherein $n$ is 0, 1 or 2, $R_1$ represents hydrogen, alkyl, acyl or furfuryl and $R_2$ stands for hydrogen or methyl with the proviso that $R_1$ and $R_2$ cannot both be methyl if $n$ is 0;

wherein R stands for hydrogen, alkyl, furfuryl or acyl.

Illustrative examples of compounds corresponding to formulae (1) and (2) include:

| (1) a. (2-methylpyrazinyl-3, -5 and -6) furfuryl sulfide | n.c. |
| b. pyrazinylmethyl-mercaptan | n.c. |
| c. pyrazinylmethyl methyl sulfide | n.c. |
| d. pyrazinylmethyl ethyl sulfide | n.c. |
| e. pyrazinylmethyl furfuryl sulfide | n.c. |
| f. pyrazinylmethylthiol acetate | n.c. |
| g. 2-pyrazinyl-ethyl mercaptan | n.c. |
| h. 2-pyrazinyl-ethyl methyl sulfide | n.c. |
| i. 2-pyrazinyl-ethyl ethyl sulfide | n.c. |
| j. 2-pyrazinyl-ethyl furfuryl sulfide | n.c. |
| k. 2-pyrazinyl-ethylthiol acetate | n.c. |
| (2) a. 2,5-dimethyl-3-mercapto-pyrazine | n.c. |
| b. 2,5-dimethyl-3-methylthio-pyrazine | n.c. |
| c. 2,5-dimethyl-3-ethylthio-pyrazine | n.c. |
| e. 2,5-Dimethyl-3-acetylthio-pyrazine | n.c. |
| d. 2,5-dimethyl-3-furfurylthio-pyrazine | n.c. |

The new compounds included in this group can be obtained as follows:

(1) a. (2-Methylpyrazinyl-3, -5 and -6) furfuryl sulfide (mixture): a mixture of 2-methyl-3-, 5- and 6-chloropyrazine was prepared by chlorination of 2-methylpyrazine according to the method described in J. Org. Chem. 26, 2356, 2360 (1961). 0.2 Mole of the above 2-methyl-chloropyrazine mixture was added to 0.2 mole of a sodium furfurylmercaptide suspension in 250 ml. of xylene. The mixture was boiled for 6 hours. After cooling 250 ml. of water were added, the organic layer was concentrated and distilled. 13.5 g. of a mixture of (2-methylpyrazinyl-3, -5 and -6) furfuryl sulfide were obtained; b.p. 153°–156° C./10 Torr; $n_D^{20} = 1.5970$; $d_4^{20} = 1.2164$.

(1) b. Pyrazinylmethylmercaptan: a solution of 6.3 g. (0.05 mole) of chloromethylpyrazine [obtained according to the method described in J. Org. Chem. 26, 2356 (1961)] in 20 ml. of ether was added slowly, with stirring, to a solution of sodium hydrogensulfide (60%) in 50 ml. of absolute methanol. Stirring of the reaction mixture at room temperature was continued for 3 hours. The precipitate which had formed was removed by filtering, the solvents were evaporated, and the residue was dissolved in water. The solution was extracted twice with ether. The aqueous phase was neutralized with acetic acid and extracted with ether. After drying of the extract the solvent was evaporated and the residue distilled. 0.25 g. of pyrazinylmethylmercaptan boiling at 44°–45° C./0.07 mm. Hg. was obtained.

(1) c. Pyrazinylmethyl methyl sulfide was prepared according to the method described in Houben-Weyl, 4th ed., vol. 9, 97 (1955) by reacting chloromethylpyrazine [obtained by the method described in J. Org. Chem. 26, 2356 (1961)] with sodium methylmercaptide. The product has a b.p. of 105°–106° C./12 mm. Hg.

(1) d. Pyrazinylmethyl ethyl sulfide was prepared by the same method as used for compound (1) c., except that sodium ethylmercaptide was used in place of sodium methylmercaptide. The product has a b.p. of 114°–116° C./12 mm. Hg.

(1) e. Pyrazinylmethyl furfuryl sulfide was prepared by the same method as used for compound (1) c., except that sodium furfurylmercaptide was used instead of sodium methylmercaptide. The product has a b.p. of 116° C./0.05 mm. Hg.

(1) f. Pyrazinylmethylthiol acetate was prepared by acetylation of pyrazinylmethylthiol according to the method described in Houben-Weyl, 4th, ed., vol. 9, 753 (1955). The product has a b.p. of 52° C./0.02 mm. Hg.

(1) g. 2-Pyrazinyl-ethyl mercaptan was prepared by reacting vinylpyrazine [obtained by the method described in J. Org. Chem. 27, 1363 (1962)] and hydrolyzing the resulting thiolic acid ester according to the method described in J. Org. Chem. 22, 980 (1957). The product has a b.p. of 56.5°–60° C./0.003 mm. Hg.

(1) h. 2-Pyrazinyl-ethyl methyl sulfide was prepared by reacting vinylpyrazine [c.f. J. Org. Chem. 27, 1363 (1962] with methylmercaptan by the action of ultra violet light and in the presence of benzoyl peroxide by the method described in Acta Chem. Scand. 8, 295 (1954). The product was identified by mass spectrometry. It has a b.p. of 57°–69° C. at 0.05 mm. Hg.

(1) i. 2-Pyrazinyl-ethyl ethyl sulfide was prepared by the method used for compound (1) h., but using ethylmercaptan. It has a b.p. of 75° C./0.03 mm. Hg.

(1) j. 2-Pyrazinyl-ethyl furfuryl sulfide was prepared by the method used for compound (1) h., but using furfuralmercaptan. The product has a b.p. of 116°–117° C./0.01 mm. Hg.

(1) k. 2-Pyrazinyl-ethylthiol acetate was prepared by reacting vinylpyrazine with thioacetic acid in the presence of benzoyl peroxide as a catalyst according to the method described in J. Org. Chem. 27, 2853 (1962). The product has a b.p. of 80° C./0.02 mm. Hg. (2) a. 2,3-Dimethyl-3-mercapto-pyrazine: A solution of 1.3 g. (0.023 mole) of sodium hydrogensulfide and 2.5 g. (0.01 mole) of 2,5-dimethyl-3-iodo-pyrazine in 70 ml. of absolute methanol was refluxed for 3 hours. After evaporation of the alcohol the residue was dissolved in 1-n NaOH, the solution was filtered and the filtrate was neutralized with acetic acid. After isolation by the usual treatments the reaction product was sublimated. There was obtained 0.81 g. of a yellow powder having a m.p. of 182°–185° C.

(2) b. 2,5-Dimethyl-3-methylthio-pyrazine: 2.85 g. (0.02 mole) of 2,5-dimethyl-3-chloropyrazine and 0.06 mole of methylmercaptan were dissolved in a solution of 0.7 g. of sodium in 20 ml. of absolute ethanol. The reaction mixture was refluxed for 45 minutes. After removal of the alcohol by distillation the residue was dissolved in water and the sulfide was extracted with ether and distilled. The product (yield 75.6%) has a b.p. of 40°–50° C./11 mm. Hg.

(2) c. 2,5-Dimethyl-3-ethylthio-pyrazine was prepared in the same manner as compound (2) b., except that 0.06 mole of ethylmercaptan was used instead of methylmercaptan. The product (yield 75%) has a b.p. of 128° C./9 mm. Hg.

(2) d. 2,5-Dimethyl-3-furfurylthio-pyrazine was prepared in the same manner as compound (2) b., except that 0.06 mole of furfurylmercaptan was used instead of methylmercaptan. The product (yield 75%) has a b.p. of 115°–120° C./0.02 mm. Hg.

(2) e. 2,5-Dimethyl-3-acetylthio-pyrazine was prepared by acetylating 2,5-dimethyl-3-mercapto-pyrazine [compound (2) a.] with acetic anhydride in an alkaline medium according to the method described in Houben-Weyl, 4th ed., vol. 9, 753 (1955). The product has a m.p. of 36°–42° C.

Organoleptic evaluation test data are reported in TABLE XXXV below.

XXXVI — Phenols and Phenol Ethers

The compounds of this group can be represented by the following general formulae:

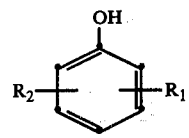

wherein $R_1$ represents alkyl or acetyl and $R_2$ represents hydrogen or methyl, with the proviso that $R_1$ and $R_2$ together comprise at least 2 carbon atoms;

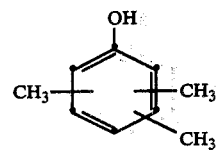

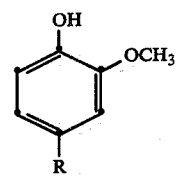

wherein R represents alkyl.

Examples of compounds defined by the above formulae:

| (1), (2) and (3) include: | |
|---|---|
| (1) a. 2-ethyl-phenol | o.a. |
| b. 3-ethyl-phenol | o.a. |
| (1) c. 4-ethyl-phenol | o.a. |
| d. 4-isopropyl-phenol | Compt.rend. 177, 453 (1923) |
| e. 2,3-xylenol | o.a. |
| f. 2,4-xylenol | o.a. |
| g. 2,5-xylenol | o.a. |
| h. 2,6-xylenol | o.a. |
| i. 3,4-xylenol | o.a. |
| j. 3,5-xylenol | o.a. |
| k. 2-hydroxy-acetophenone | o.a. |
| l. 2-hydroxy-propiophenone | Org.Synth.13, 90 (1933) |
| m. 4-hydroxy-propiophenone | Org.Synth.13, 90 (1933) |
| n. 5-methyl-2-hydroxy-acetophenone | Ann. 460, 83 (1927) |
| (2) a. 2,3,5-trimethyl-phenol | o.a. |
| b. 2,4,6-trimethyl-phenol | o.a. |
| c. 2,4,5-trimethyl-phenol | o.a. |
| d. 3,4,5-trimethyl-phenol | o.a. |
| (3) a. 4-ethyl-2-methoxy-phenol | o.a. |
| b. 4-propyl-2-methoxy-phenol | Helv. 8, 334 |

-continued (1925)

wherein $R_1$ is alkyl and $R_2$ stands for alkyl or furfuryl.

Specific compounds included in the above formulae are:

| | | | |
|---|---|---|---|
| (1) | a. | thiophane-3-one | J.A.C.S. 68, 2229 (1946) |
| | b. | 2-methyl-thiophane-3-one | Helv. 27, 124 (1944) |
| (2) | a. | 2,6-dimethyl-gamma-pyrone | Ber. 69, 2379 (1936) |
| | b. | 2,6-dimethyl-thio-gamma-pyrone | Ber. 52, 1539 (1919) |
| | c. | 2,6-dimethyl-dithio-gamma-pyrone | Compt. rend. 238, 1717 (1954) |
| (3) | a. | furfurylthioacetone | n.c. |
| | b. | 1-methylthio-butan-2-one | n.c. |
| (3) | c. | methylthioacetone | J.A.C.S. 76, 164 (1954) |
| (4) | A. | dimethylmercaptal of α-methylbutanal | n.c. |
| | b. | difurfurylmercaptal of α-methylbutanal | n.c. |
| | | The present group also includes: | |
| (5) | a. | 5-methyl-furyl-2-nitrile | J.A.C.S. 54, 2549 (1932) |

The present group also comprises the single compound (4) a. 4-vinyl-1,2-dimethoxy-benzene.

Evaluation test data are set out in TABLE XXXVI below.

XXXVII — Aliphatic Oxoalcohols

This group comprises compounds having the general formula

R—CO—CH$_2$OH    (1)

wherein R stands for alkyl. Examples of compounds corresponding to this definition include:

| | |
|---|---|
| (1) a. 2-Oxo-propan-1-ol | Ann. 596, 61 (1955) |
| (1) b. 2-oxo-butan-1-ol | Ann. 596, 68 (1955) |

Flavor evaluation data are set out in TABLE XXXVII below.

XXXVIII — Miscellaneous

This group comprises compounds of the classes represented by the following general formulae:

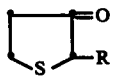    (1)

wherein R stands for hydrogen, methyl or ethyl;

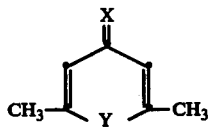    (2)

wherein each of the symbols X and Y represents oxygen or sulfur;

$R_1$—CH$_2$COCH$_2$S—R$_2$    (3)

wherein $R_1$ represents hydrogen or alkyl and $R_2$ stands for alkyl or furfuryl;
and

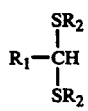    (4)

The new compounds included in this group XXXVIII can be obtained as follows:

(3) a. Furfurylthioacetone was prepared in the same manner as methythioacetone [cf. compound (3) c.] according to the method described in J.A.C.S. 76, 114 (1954) by condensing 0.122 mole of chloroacetone with 0.11 mole of sodium furfurylmercaptide. After the usual separation and purification of the reaction product there were obtained by distillation 13.9 g. of pure furfurylthioacetone distilling at 115°–177° C./10 Torr. $n_D^{22.8}$ = 1.5250; $d_4^{23}$ = 1.150.

(3) b. 1-Methylthio-butan-2-one was prepared in the same manner as methylthioacetone according to the method described in J.A.C.S. 76, 114 (1954) by condensing 0.122 mole of 1-chlorobutan-2-one [obtained according to the method described in Ber. 82, 229 (1949)] with 0.11 mole of sodium methylmercaptide. The reaction product was separated by filtration from the NaCl formed in the reaction and concentration of the filtrate. By distillation of the residue there were obtained 8.2 g. of pure 1-methylthiobutan-2-one distilling at 52°–53° C./8 Torr. $n_D^{22}$ = 1.4700; $d_4^{22}$ = 0.9970.

(4) a. Dimethylmercaptal of α-methylbutanol: Dry HCl was introduced into a mixture of 0.05 mole α-methylbutanal and 0.11 mole methanthiol. By cooling the temperature was maintained between 0° and 5° C. After 15 minutes 50 ml. of water were added, the mixture extracted with ether, the ether layer washed with a NaHCO$_3$ solution and water. By distillation of the ether concentrate 4.2 g. of dimethylmercaptal of α-methylbutanal were obtained; b.p. 75°–76° C./8 Torr; $n_D^{24}$ = 1.5050; $d_4^{24}$ = 0.9761.

(4) b. Difurfurylmercaptal of α-methylbutanal: This compound was prepared by the same method as compound (4) a., using 0.11 mole of furfurylmercaptan instead of methanthiol. 6.4 g. of difurfurylmercaptal were obtained; b.p. 130° C./0.1 Torr; $n_D^{22.8}$ = 1.5500; $d_4^{23}$ = 1.126.

Organoleptic evaluation as flavor agents gave the results set out in TABLE XXXVIII below.

ORGANOLEPTIC EVALUATIONS

As was described above, the compounds of this invention were subjected to organoleptic evaluation tests either in a syrup base (A), or one of the two soluble coffee bases (B and C). The following tables give the results of these organoleptic evaluations. In the tables, the Roman numeral refers to the number of the group from which the test compounds were selected. The column headed "Number" refers to the number of the test compound of the corresponding group. The column headed "Test" gives the Method of the Test, as described hereinbefore, and the column headed "Quantity" sets out the amount of the Test Compound used in grams per 100 liters of the base material.

ORGANOLEPTIC EVALUATION TABLES

| Number | Test | Quantity | Organoleptic Characterization |
|---|---|---|---|
| TABLE I | | | |
| (1)a. | A | 0.2 | neroli-, bergamot- and cinnamon-like; natural note |
| (1)b. | A | 0.05 | green note |
| (1)c. | A | 0.15 | green note; rose-like |
| (1)d. | A | 1 | grape- and fig-like |
| (1)d. | C | 0.03 | winey, buttery, woody, nutty |
| (1)e. | A | 5 | green, metallic taste |
| TABLE II | | | |
| (1)a. | A | 0.05 to 0.1 | green, musty taste |
| (1)b. | A | 0.1 | oily, aromatic |
| (1)c. | A | 0.15 | oily taste |
| (1)D. | A | 0.15 | aromatic taste |
| (1)e. | A | 1.0 | aromatic taste |
| (1)f. | A | 0.25 | mouldy, tarry taste |
| (1)g. | A | 1.0 | mouldy, aromatic taste |
| (1)h. | A | 0.25 | aromatic taste |
| (1)i. | A | 1.0 | earthy taste |
| (1)j. | A | 2.0 | sweet, anise- and honey-like taste |
| (1)k. | A. | 0.5 | strawberry-like |
| (1)l. | A | 0.25 | earthy taste |
| (1)m. | A | 1 | slightly fruity; dry |
| (1)n. | A | 0.15 | fatty, earthy taste |
| (1)c. | A | 0.25–0.50 | aromatic taste |
| (1)p. | A | 1.0 | aromatic earthy taste |
| TABLE III | | | |
| (1)a. | A | 0.5 | phenolic; coffee-grounds |
| (1)a. | B | 0.5–1.0 | enhancement of the roasted note |
| (1)a. | C | 0.68 | grounday; cereal-like |
| (2)a. | A | 0.05 | styrene-like; aromatic |
| (2)b. | A | 1–3 | slightly phenolic; burnt taste |
| (2)b. | B | 0.4 | enhancement of the bitter note |
| (2)c. | A | 0.3 | salicylate-like taste |
| (2)d. | A | 0.25 | earthy flavor note |
| (2)e. | A | 1.0 | burnt, caramel taste |
| (2)f. | A | 0.25 | phenolic; saffron-like |
| (2)g. | B | 0.12 | earthy; mushroom-like; hazelnut |
| (2)h. | B | 0.50 | burnt; green-taste |
| (2)i. | B | 0.095 | earthy flavor note |
| (3)a. | A | 1.0 | aromatic taste |
| (3)a. | C | 0.1 | medicinal; camphor; rioy |
| (3)b. | A | 1.0 | green-cooked taste |
| (3)a. | C | 0.11 | liquorice-like; sen-sen |
| (3)c. | A | 2.0 | green-owdery taste |
| (3)c. | C | 0.068 | bitter; wintergreen mouthfeel |
| TABLE IV | | | |
| (1)a. | B | 0.75 | roasted; bitter; green |
| (1)a. | C | 1.1 | nitrobenzene-like |
| (1)b. | B | 0.85 | fatty; winey |
| (1)c. | A | 1.0 | styrene-like |
| (1)d. | A | 0.5 | styrene-like |
| (1)e. | A | 1.0 | chemical-like taste |
| (1)f. | A | 0.1 | styrene-like |
| (1)g. | C | 0.11 | hydrocarbon like |
| (1)h. | A | 0.1 | burnt; horn-like; methyl furoats-like |
| (1)h. | C | 0.54 | solvent; latex paint-like |
| (1)i. | A | 1.0 | diphenyloxide-like |
| (1)j. | A | 1.0–2.0 | onion-like |
| (1)k. | A | 1.0 | green taste |
| (2)a. | A | 0.05 | styrene-like |
| (2)a. | C | 0.01 | sulfury; nutty; buckwheat-like |
| (3)a. | A | 0.25 | fruity, green |
| (3)a. | C | 0.01 | geranium, metallic; acid; sulfury |
| (3)b. | A | 1.0 | fruity taste |
| (3)c. | A | 0.5 | green taste |
| (3)c. | C | 0.068 | apricot, medicinal; sulfury; sour |
| (3)d. | A | 1.0 | dry fuit flavor |
| (4)a. | A | 0.025 | dry phenolic taste |
| (4)a. | B | 0.042 | modified phenolic note |
| (4)a. | C | 0.042 | iodoform; sulfury |
| (4)b. | A | 1.0 | fruity; green taste |
| (5)a. | B | 0.006 | hydrocarbon; rubbery; earthy |
| (5)b. | B | 0.12 | hydrocarbon; phenolic |
| TABLE V | | | |
| (1)a. | A | 0.2 | burnt taste |
| (1)b. | A | 0.1 | green, fatty taste |
| (1)c. | A | 0.03 | fatty taste |
| (1)c. | C | 0.021 | aldehyde like |
| (1)d. | A | 0.1 | green taste |
| (2)a. | A | 2.0 | fruity taste |
| (2)a. | C | 0.016 | earthy, mushroom-like |
| (2)b. | A | 0.25 | gooseberry-like |
| (2)b. | C | 0.013 | geranium; green; rubbery; sulfury |
| TABLE VI | | | |
| (1)a. | B | 0.6 | astringent; hazel-nut; basic taste |
| (1)b. | B | 0.25 | green; earthy; hazel-nut-like |
| (1)c. | A | 0.25 | caramel-like - roasted hazel-like taste |
| (1)c. | C | 0.096 | buttery; green; cereal; caramel |
| (1)d. | A | 0.5 | green; melon-like taste |
| (1)e. | A | 0.5–1.0 | fatty taste |
| (1)f. | A | 0.25 | green, burnt, coffee-like |
| (1)g. | A | 0.25 | green, fruity, strawberry-like melon-like taste |
| (1)h. | A | 0.3 | fatty; green |
| (1)i. | A | 0.6 | coffee-like |
| (1)i. | B | 0.5 | roasted, rubbery |
| (1)j. | A | 1.0 | green |
| (1)j. | B | 1.0 | basic; bitter; astringent |
| (1)k. | A | 0.3 | rum-like; |
| (1)k. | B | 0.15 | roasted; green; earthy |
| (1)l. | A | 1.0 | green |
| (1)l. | B | 0.2 | green; astringent; earthy |
| (1)m. | A | 2.0 | green |
| (1)m. | B | 0.6 | almond-like; |
| (1)n. | A | 0.8 | green; fatty; roasted |
| (1)n. | B | 0.25 | basic; green; hazelnut-like |
| (1)o. | A | 0.2 | green |
| (1)o. | B | 0.13 | astringent, roasted; hazelnut |
| (1)p. | B | 0.6 | basic; green |
| (1)q. | B | 0.25 | bitter; earthy; roasted |
| (1)r. | B | 0.3 | bitter; caramel |
| (1)s. | B | 0.75 | bitter; basic |
| (1)t. | B | 0.45 | green; astringent |
| (1)u. | C | 0.054 | winey; buttery; acid; cereal-like sulfury; caramel; solvent-like |
| TABLE VII | | | |
| (1)a. | A | 0.3 | burnt, hardnut taste |
| (1)a. | B | 0.4 | enhanced the woody and coffee grounds note |
| (1)b. | A | 0.5 | green, vegetable-like |
| (1)b. | C | 0.17 | earthy, potato-like |
| (1)c. | A | 0.5 | earthy flavor |
| (1)c. | C | 0.2 | green; nitrobenzene |
| (1)d. | A | 0.5 | earthy, potato-like |
| (1)d. | B | 0.1–0.2 | enhanced the woody and coffee grounds notes; adds a bitter note |
| (1)d. | C | 0.084 | earthy; green; sulfury; mouthfeel |
| (1)e. | A | 0.25 | anise-like, liquorice flavor |
| (1)f. | A | 1.0 | hazelnut, coffee-like |
| (1)g. | A | 0.5 | anise-like |
| (1)h. | A | 2.0 | slight caramel flavor |
| (1)i. | A | 0.1 | earthy; potato; hazelnut taste |
| (1)i. | B | 0.01–0.02 | enhanced the coffee grounds note |
| (1)i. | C | 0.013 | earthy; green; acid |
| (1)j. | B | 0.06 | earthy; hazelnut; burnt taste |
| (1)k. | B | 0.45 | sweet; green; burnt; astringent note |
| (1)l. | A | 2.0 | earthy note |
| (1)m. | A | 4.0 | burnt; praline-like |
| (1)n. | A | 1.0 | green; burnt note |
| (1)o. | A | 4.0 | slight coffee taste; caramel; fruity |
| (1)p. | A | 4.0 | green, burnt note |
| (1)q. | A | 2.0 | burnt; coffee-like note |
| (1)r. | A | 0.3 | fresh; hazelnut; earthy note |
| (1)r. | C | 0.07 | earthy; green note |
| (2)a. | A | 3.0 | coffee-like taste |
| (2)b. | A | 0.5 | burnt almond taste |
| (2)b. | B | 0.2–0.4 | enhanced woody note |
| (2)c. | A | 2.0 | hazelnut taste |
| (2)d. | A | 4.0 | mild hazelnut taste |
| (2)e. | A | 1.0 | coffee-like taste |
| (2)e. | B | 1.0 | enhanced green and nutty notes |
| (2)f. | A | 3.0 | hazelnut, slightly burnt taste |
| (2)g. | A | 2.5 | caramel-like, fruity taste |
| (2)h. | A | 0.5 | green foral taste |
| (2)i. | A | 1.0 | anise-like taste |
| (2)j. | A | 0.5 | hazelnut-like taste |
| (3)a. | A | 1.0 | burnt, roasted hazelnut-like taste |
| (3)a. | C | 0.27 | toasted |
| (3)b. | A | 4.0 | phenolic, burnt taste |
| (3)c. | A | 4.0 | burnt, earthy taste |
| (3)d. | B | 2.5 | astringent; fatty; earthy |
| (3)e. | B | 0.7 | hazelnut-like; bitter; roasted |
| (3)f. | B | 0.6 | bitter; earthy |
| (3)g. | B | 2.5 | bitter; acrid; earthy |
| (3)h. | B | 1.2 | bitter; astringent |
| (3)i. | B | 2.5 | bitter; acid; woody |
| (3)j. | B | 1.2 | bitter; earthy; woody |
| (3)k. | B | 1.2 | bitter; earthy; fatty |
| (3)l. | B | 2.0 | green; roasted |
| (4)a. | A | 2.0 | roasted hazelnut-like taste |
| (4)b. | A | 1.0 | burnt, hazelnut-like taste |
| (4)b. | B | 1.0 | enhanced the green nutty note |

-continued

| Number | Test | Quantity | Organoleptic Characterization |
|---|---|---|---|
| (4)c. | A | 0.5 | hazelnut-like taste |
| (4)d. | A | 4.0 | fresh hazelnut taste |
| (5)a. | A | 1.5 | caramel- and coffee-like |
| (5)b. | A | 1.5 | anise-like, floral taste |
| (5)c. | A | 3.0 | hazelnut; slightly acid |
| (5)d. | A | 3.0 | burnt, phenolic taste |
| (5)e. | A | 4.0 | fatty taste |
| (5)f. | A | 3.0 | maple-like taste |
| (5)g. | A | 1.0 | fatty taste, slightly reminiscent of chocolate |
| (5)h. | A | 1.0 | green fatty, burnt taste |
| (5)i. | A | 5.0 | fatty, hazelnut-like taste |
| (5)j. | A | 1.0 | coffee-like; green; earthy |
| (6)a. | A | 2.0 | coffee-like taste |
| (6)b. | A | 0.5 | green taste |
| (6)c. | A | 1.0 | hazelnut-like taste |
| (6)d. | A | 1.0 | coffee-like taste |
| TABLE VIII | | | |
| (1)a. | A | 5.0 | fruity taste |
| (1)b. | A | 5.0 | fruity taste |
| (1)c. | A | 0.5–1.0 | green, fruity taste |
| (1)d. | A | 0.5 | green, fatty taste |
| (1)e. | A | 0.1 | fruity, fatty taste |
| (1)f. | A | 0.1 | fatty, orange-like taste |
| (1)g. | A | 0.1 | fatty, orange-like taste |
| (1)h. | B | 0.06 | earthy, green taste |
| (1)i. | B | 0.06 | green, fatty taste |
| (2)a. | A | 0.2 | flowery taste |
| (2)b. | B | 0.9 | winey, woody, green note |
| (2)c. | B | 1.25 | spicy taste |
| (2)d. | A | 0.5 | fruity, aromatic taste |
| (2)e. | A | 0.5 | fruity taste |
| (2)f. | A | 0.5 | fruity taste |
| (2)g. | A | 4.0 | sweet, slightly fatty taste |
| (2)h. | A | 4.0 | sweet, slightly fatty taste |
| (2)i. | A | 4.0 | chocolate-like taste |
| (2)j. | A | 4.0 | chocolate-like taste |
| TABLE IX | | | |
| (1)a. | A | 1.0 | strong mustard taste |
| (1)a. | B | 1.0 | nutty, coffee grounds-like |
| (1)a. | C | 0.27 | sulfury, rioy, phenolic taste |
| (1)b. | A | 1.0 | mustard taste |
| (1)b. | C | 0.08 | buttery, grounday taste |
| (1)c. | A | 0.25–0.5 | honey-like |
| (1)c. | B | 1.0 | coffee-grounds note |
| (1)c. | C | 0.04 | rye bread, caraway seed-like |
| (1)d. | A | 1.0 | green, water-cress like |
| (1)d. | C | 0.68 | earthy, mushroom like |
| (1)e. | A | 1.0 | salicylate; coffee-like |
| (1)e. | C | 0.14 | mushroom-like |
| TABLE X | | | |
| (1)a. | A | 1.0 | mustard-like taste |
| (1)b. | A | 1.0 | fruity, woody note |
| (1)c. | A | 1.0 | woody, green, elderberry-like |
| TABLE XI | | | |
| (1)a. | A | 1.0 | green taste |
| (1)b. | A | 1.0 | fruity, woody taste |
| (1)c. | A | 1.0 | woody, green elderberry taste |
| (1)d. | A | 5.0 | slightly woody, green taste |
| TABLE XII | | | |
| (1)a. | A | 0.3 | burnt, mustard-like taste |
| (1)b. | A | 0.1 | leathery taste |
| (1)b. | B | 0.006 | green, basic taste |
| (1)c. | A | 4.0 | caramel-like |
| (1)d. | A | 1.0 | roasted, hazelnut-like |
| (1)e. | A | 4.0 | roasted, moldy flavor |
| (1)f. | B | 7.0 | bitter, green taste |
| (1)g. | B | 1.9 | hazelnut- coffee-like taste |
| (1)h. | B | 6.0 | bitter, burnt, coffee-like |
| (1)i. | A | 5.0 | paper-like taste |
| (1)i. | B | 5.0 | green, roasted taste |
| (1)j. | B | 0.3 | bitter, astringent, basic taste |
| TABLE XIII | | | |
| (1)a. | B | 15.0 | sweet, slightly basic taste |
| (1)b. | B | 0.40 | astringent, bitter, roasted note |
| (1)c. | B | 0.75 | bitter, fruity, anise-like taste |
| TABLE XIV | | | |
| (1)a. | A | 1.0 | tonka-bean like taste |
| (1)a. | C | 0.8 | nutty, bitter almond taste |
| (1)a. | B | 0.4 | bitter almond, flowery note |
| (1)b. | C | 0.08 | nutty, bitter almond taste |
| (1)c. | B | 0.25 | bitter, earthy taste |
| TABLE XV | | | |
| (1)a. | A | 1.0 | Hazelberry taste |
| (1)b. | A | 1.0 | Cherry-like taste |
| (1)b. | C | 0.27 | bitter almond, cherry-like |
| (1)c. | A | 1.0 | saffron taste |
| (1)c. | C | 0.14 | camphor note |
| (1)d. | A | 1.0 | caramel taste |
| (1)e. | A | 1.0 | burnt caramel taste |
| (2)a. | B | 0.06 | almond, caramel, buttery taste |
| (2)b. | B | 0.4 | earthy, roasted, sweet aromatic taste |
| (2)a. | C | 0.07 | nutty, starchy taste |
| TABLE XVI | | | |
| (1)a. | A | 2.0 | burnt taste |
| (1)a. | B | 1.0 | burnt, roasted flavor |
| (1)b. | A | 1.0 | mint taste |
| (1)c. | C | 0.16 | bready taste |
| (1)d. | A | 1.0 | honey-like taste with anise note |
| (1)e. | A | 0.5 | fatty, green, caraway-like taste |
| (1)f. | A | 1.0 | slight mint taste |
| (1)g. | A | 3.0 | earthy taste |
| (1)h. | A | 4.0 | slightly burnt taste, slightly acid |
| (1)i. | B | 1.2 | astringent, bitter taste |
| (1)i. | C | 1.35 | cereal-like, metallic taste |
| (1)j. | A | 3.0 | earthy taste |
| (1)j. | C | 0.54 | caramel taste |
| (1)k. | A | 1.0 | fatty, flowery taste |
| TABLE XVII | | | |
| (1)a. | A | 5.0 | bread-like taste |
| (1)a. | B | 1.25 | roasted note |
| (1)b. | B | 0.2 | hazelnut, roasted, caramel note |
| (1)c. | A | 5.0 | slight hazelnut note |
| TABLE XVIII | | | |
| (1)a. | A | 0.5 | fruity, caramel-like note |
| (1)b. | A | 0.5 | fruity note |
| (1)c. | A | 0.2 | fruity, cherry note |
| (1)j. | B | 0.06 | green note |
| (1)e. | A | 0.1 | fruity, fatty note |
| (1)f. | A | 0.1 | fatty note |
| (1)g. | A | 0.1 | fatty note |
| (1)h. | A | 0.1 | fruity note |
| (1)i. | B | 0.45 | mushroom, earthy note |
| (1)j. | A | 2.0 | fruity note |
| (1)k. | A | 2.0 | fruity note |
| (1)l. | A | 2.0 | acetone-like |
| (1)m. | A | 0.1 | sweet taste |
| (1)n. | B | 0.45 | fruity taste |
| (1)o. | A | 0.05 | green taste |
| (1)p. | B | 1.5 | almond-like taste |
| (1)q. | B | 0.125 | earthy, green note |
| TABLE XIX | | | |
| (1)a. | A | 7.0 | slight caramel-like taste |
| (1)b. | A | 4.0 | slight fruity taste |
| (1)c. | A | 4.0 | fruity taste |
| (1)d. | A | 4.0 | fruity, cheesy note |
| (1)e. | A | 4.0 | light burnt taste |
| (1)e. | C | 0.67 | nutty, starchy taste |
| (1)f. | A | 3.0 | green, hazelnut-like taste |
| (1)g. | A | 2.0 | green, burnt taste |
| (1)g. | B | 4.0 | astringent note |
| (1)g. | C | 3.46 | peach pit, almond taste |
| (1)h. | A | 6.0 | slight rum-like taste |
| (1)i. | A | 2.0 | fatty, green taste |
| (1)i. | C | 0.54 | nutty, spicy |
| (1)j. | A | 3.0 | green taste |
| (1)k. | A | 5.0 | weak furanic note |
| (1)k. | C | 0.63 | fruity, banana oil flavor note |
| (1)l. | A | 5.0 | weak furanic note |
| (1)l. | B | 1.0 | bitter, roasted note |
| (1)l. | C | 1.35 | acid flowery note |
| (1)m. | A | 5.0 | sweet aromatic taste |
| TABLE XX | | | |
| (1)a. | A | 1.0 | onion-like taste |
| (1)a. | B | 0.5–1.0 | malty, roasted note |
| (1)b. | A | 0.25 | sweet honey-like taste |
| (1)b. | C | 0.11 | nutty, starchy taste |
| (1)d. | A | 1.0 | burnt anthranilate-like taste |
| (1)e. | A | 1.0 | nonalactone-like taste |
| (1)f. | A | 1.0 | wine-like taste |
| (1)g. | A | 1.0 | sweet, flowery taste |
| (1)h. | A | 2.0 | cream, caramel-like taste |
| (1)i. | A | 2.0 | green, mustard-like note |
| (2)a. | A | 4.0 | sweet note |
| (2)b. | A | 5.0 | slightly roasted note |
| TABLE XXI | | | |
| (1)a. | A | 2.0 | fruity, rose-like taste |
| (1)b. | A | 0.5 | green taste |
| (1)c. | A | 3.0 | green taste |
| (1)e. | C | 0.025 | geranium taste |
| (2)a. | B | 0.60 | astringent, bitter, roasted taste |
| (2)a. | C | 1.35 | fermented taste |
| (2)b. | B | 0.20 | astringent, peanut, roasted taste |
| (3)a. | B | 0.60 | bitter, earthy, roasted taste |
| (3)b. | A | 1.00 | grape-like taste |
| (3)b. | B | 0.06 | fatty, bitter, roasted taste |
| (3)b. | C | 0.06 | starchy taste |
| (4)a. | A | 4.0 | weak, sweet taste |
| (4)b. | A | 2.0 | woody taste |

| Number | Test | Quantity | Organoleptic Characterization |
|---|---|---|---|
| TABLE XXII | | | |
| (1)a. | A | 2.0 | anthranilic, burnt flavor |
| (1)b. | A | 3.0 | fruity, burnt taste |
| (1)c. | A | 0.5 | burnt nutty taste |
| (1)c. | C | 0.034 | toasted, unroasted coffee bean note |
| (1)d. | A | 3.0 | green, grapefruit taste |
| TABLE XXIII | | | |
| (1)a. | A | 0.12 | roasted, coffee-like |
| (1)a. | B | 0.08 | hazelnut, coffee-like |
| (1)b. | A | 2.5 | chocolate-like |
| (1)b. | C | 1.18 | sulfury, starch-like |
| (1)c. | A | 5.0 | burnt, roasted note |
| (1)c. | B | 3.0 | phenolic, basic taste |
| (1)d. | B | 7.5 | burnt, coffee-like taste |
| (1)e. | A | 4.0 | caramel, fatty taste |
| (1)e. | B | 5.5 | bitter, green taste |
| (1)f. | B | 7.5 | bitter, astringent note |
| (1)g. | A | 5.0 | fruity taste |
| (1)h. | A | 4.0 | caramel, fruity taste |
| (1)i. | B | 2.0 | bitter, musty taste |
| (1)j. | B | 2.5 | green, woody, fruity note |
| (1)k. | B | 45.0 | astringent, bitter, musty taste |
| (1)l. | B | 5.5 | bitter, coffee-like taste |
| (1)m. | B | 3.0 | earthy taste |
| TABLE XXIV | | | |
| (1)a. | A | 1.0 | fruity, pear-like taste |
| (1)a. | B | 0.125 | green, chocolate cream-like taste |
| (1)b. | A | 3.0 | burnt buttery rum note |
| (1)c. | A | 3.0 | strawberry-like taste |
| (1)d. | A | 1.0 | caramel-like taste |
| (1)d. | C | 0.07 | acid, fermented taste |
| (1)e. | A | 1.0 | caramel-like, cocoa taste |
| (1)e. | C | 0.34 | whey, nutty taste |
| (1)f. | A | 2.0 | fruity, butter-like taste |
| (1)g. | A | 0.5 | fruity (melon, pear-like) taste |
| (1)h. | B | 0.1 | caramel, pineapple taste |
| (1)i. | A | 1.0 | fatty, rancid note |
| (2)a. | A | 1.0 | caramel-nutty taste |
| (2)a. | C | 0.41 | fruity, pineapple note |
| (2)b. | A | 2.0 | fruity taste |
| (2)c. | A | 2.0 | fruity taste |
| (2)d. | A | 0.5 | fruity taste |
| TABLE XXV | | | |
| (1)a. | A | 1.0 | praline-like taste |
| (1)a. | B | 2.0 | woody, coffee grounds note |
| (1)b. | A | 2.0 | fruity taste |
| (1)c. | A | 1.0 | egg-like taste |
| (1)c. | B | 0.2–0.4 | woody note |
| (1)d. | B | 1.9 | astringent, fruity, green taste |
| TABLE XXVI | | | |
| (1)a. | B | 3.0 | bitter, roasted peanut taste |
| (1)b. | B | 1.0 | buttery, slightly meaty taste |
| TABLE XXVII | | | |
| (1)a. | A | 1.0 | pear-like taste |
| (1)a. | C | 0.67 | bitter, nutty taste |
| (1)b. | A | 2.0 | gooseberry-like taste |
| (1)c. | A | 2.0 | fruity, quince-like taste |
| (1)d. | A | 2.0 | fruity taste |
| (1)e. | A | 2.0 | mushroom-like taste |
| (1)e. | C | 0.07 | earthy, mushroom-like |
| (1)f. | A | 1.0 | fruity taste |
| (1)g. | A | 1.0 | fruity taste |
| (1)h. | A | 2.0 | mushroom-like taste |
| (1)i. | B | 0.08 | fruity, hydrocarbon taste |
| (2)a. | A | 3.0 | burnt taste |
| (2)a. | C | 0.21 | buttery, vanilla-like taste |
| (2)b. | A | 3.0 | phenolic burnt note |
| (2)b. | B | 0.15 | earthy, roasted note |
| (2)c. | B | 0.20 | caraway seed note |
| (2)c. | C | 0.09 | flowery, earthy note |
| (2)d. | B | 0.09 | green, geranium note |
| (2)e. | B | 2.0 | chocolate note |
| (2)f. | A | 0.65 | sicy, winey, roasted almond taste |
| (2)g. | B | | |
| TABLE XXVIII | | | |
| (1)a. | A | 1.0 | anthranilate-like taste with burnt note |
| (1)a. | B | 0.2 | aromatic note |
| (1)a. | C | 0.135 | grape note |
| (1)b. | A | 2.0 | burnt taste |
| (1)b. | C | 0.135 | fermented grape, sour, winey note |
| (1)c. | A | 1.0 | burnt taste |
| (1)d. | A | 2.0 | oily, burnt taste |
| (1)d. | C | 0.126 | apricot, astringent, acid, sour note |
| (1)e. | A | 2.0 | oily, burnt taste |
| (1)e. | C | 0.17 | sulfury, rubbery, toasted note |
| (1)f. | A | 2.0 | earthy note |
| (2)a. | A | 1.0 | mustard-like taste |
| (2)a. | C | 0.34 | sweet, solvent-like |
| (2)b. | A | 1.0 | acetate-like taste |
| TABLE XXIX | | | |
| (1)a. | B | 4.0 | astringent, bitter taste |
| TABLE XXX | | | |
| (1)a. | A | 0.25 | roasted barley taste |
| (1)a. | B | 0.06 | roasted coffee taste |
| (1)a. | C | 0.68 | earthy, ricy taste |
| (1)b. | A | 0.1 | burnt taste |
| (1)b. | B | 0.01 | roasted flavor note |
| (1)b. | C | 0.08 | grounday, toasted, nutty note |
| (1)c. | A | 0.5 | burned, slightly rubbery note |
| (1)d. | A | 0.05 | meat broth-like |
| (1)e. | A | 0.1 | burnt taste |
| (1)f. | A | 0.05 | burnt, green, fatty taste |
| (1)g. | A | 0.5–1.0 | burnt, phenolic taste |
| (1)h. | A | 0.1 | burnt taste |
| (1)h. | B | 0.03 | bitter, roasted note |
| (1)h. | C | 0.05 | bitter, astringent taste |
| (1)i. | A | 0.01 | burnt, meat-like taste |
| (1)i. | B | 0.03 | bitter, astringent taste |
| (1)i. | C | 0.01 | sulfury brothy taste |
| (1)j. | A | 1.0 | rubbery taste |
| (1)k. | B | 0.08 | roasted taste |
| (2)a. | A | 1.0 | styrene-like taste |
| (2)b. | A | 0.75 | bitter roasted taste |
| (3)a. | A | 0.05 | burnt, flowery note |
| (3)b. | B | 0.05 | sulfurous, earthy note |
| (3)b. | C | 0.13 | nutty, mercaptan note |
| TABLE XXXI | | | |
| (1)a. | A | 0.05 | coffee taste |
| (1)a. | B | 0.04 | coffee taste |
| (1)a. | C | 0.02 | sulfury, mercaptan taste |
| (1)b. | A | 0.25 | coffee-like, alliaceous note |
| (1)c. | A | 0.25 | coffee-like |
| (1)d. | A | 1.0 | garlic-like |
| (1)e. | A | 0.25 | coffee-like |
| (1)e. | C | 0.03 | sulfury, sour, caramel, nutty flavor |
| (1)f. | A | 1.0 | coffee-like, mushroom |
| (1)g. | A | 0.1 | coffee-like |
| (1)g. | C | 0.01 | burnt, cereal, nutty taste |
| (1)h. | A | 0.01 | burnt, onion, mushroom note |
| (2)a. | A | 0.01–0.03 | mustard onion-like |
| (2)a. | B | 0.004 | bland coffee taste |
| (2)a. | C | 0.005 | geranium-like |
| (2)b. | A | 0.05 | onion-like |
| (2)c. | A | 0.05 | onion-like |
| (2)c. | B | 0.02 | astringent |
| (2)c. | C | 0.02 | nutty, astringent, bitter note |
| (2)d. | B | 0.015 | fatty, earthy taste |
| (2)d. | C | 0.013 | flowery, mercaptan taste |
| (2)e. | B | 0.002 | metallic, roasted note |
| (2)e. | C | 0.006 | woody, bitter, nutty taste |
| (2)f. | A | 0.001 | burnt, onion, caramel note |
| (3)a. | A | 0.2–0.5 | cabbage taste |
| (3)a. | C | 0.067 | sulfury, mercaptan-like |
| (4)a. | A | 0.3 | burnt coffee, metallic note |
| (5)a. | B | 0.03 | metallic, sulfurous note |
| (5)b. | B | 0.06 | metallic, astringent, earthy note |
| TABLE XXXII | | | |
| (1)a. | A | 0.01 | coffee-like |
| (1)a. | C | 0.007 | sulfurous, mercaptan |
| (1)b. | A | 0.01 | garlic-like |
| (1)c. | A | 0.1 | coffee-like |
| (1)c. | B | 0.01 | aromatic note |
| (1)c. | C | 0.005 | geranium, mercaptan, nutty note |
| (1)d. | A | 0.001 | burnt, coffee grounds, onion taste |
| (1)e. | A | 0.10 | burnt, onion taste |
| (2)a. | A | 1.0 | cooked vegetable-like taste |
| (2)b. | A | 1.0 | burnt, coffee-like taste |
| (2)c. | A | 1.0 | coffee-like |
| TABLE XXXIII | | | |
| (1)a. | A | 5.0 | fortifies the bitter taste |
| (1)a. | C | 0.093 | popcorn, nutty, caramel, cereal taste |
| (1)b. | A | 0.25 | enhances the burnt note |
| (1)c. | A | 0.25 | enhances the phenolic note |
| (1)d. | A | 5.0 | enhances the burnt note |
| (1)d. | C | 0.025 | green, acid, cereal, bitter, sour note |
| (1)e. | A | 0.2 | enhances the roast note |
| (1)f. | A | 6.0 | weak note |
| (1)g. | B | 0.30 | roasted, astringent, earthy note |
| (1)h. | B | 0.12 | mushroom, bitter, green taste |
| (1)f. | B | 0.25 | astringent, fatty, green taste |
| (1)j. | B | 0.40 | astringent, roasted taste |
| (1)k. | B | 0.40 | astringent, green note |
| (1)l. | B | 0.30 | bitter, green, earthy note |
| (1)m. | B | 0.12 | metallic note |
| (1)n. | B | 0.40 | bitter fatty note |
| TABLE XXXIV | | | |
| (1)a. | B | 0.03 | metallic, burnt note |
| (1)b. | B | 0.01 | metallic, earthy, burnt note |

-continued

| Number | Test | Quantity | Organoleptic Characterization |
|---|---|---|---|
| (1)c. | B | 0.60 | astringent, sulfurous, green note |
| (1)d. | B | 0.03 | metallic, sulfurous, burnt note |

TABLE XXXV

| Number | Test | Quantity | Organoleptic Characterization |
|---|---|---|---|
| (1)a. | A | 0.1 | roasted coffee-like taste |
| (1)a. | B | 0.1 | roasted, coffee grounds note |
| (1)b. | A | 2.0 | roasted meat-like taste |
| (1)c. | A | 0.1 | cabbage taste |
| (1)c. | B | 0.01–0.02 | strawy, dark flavor note |
| (1)d. | A | 0.2–0.3 | cabbage, onion taste |
| (1)e. | A | 2.0 | coffee-like taste |
| (1)e. | C | 0.135 | sulfury, toasted, nutty, burnt cereal note |
| (2)a. | A | 1.0 | coffee-like taste |
| (2)a. | C | 0.133 | burnt, sulfury, rubbery note |
| (2)b. | C | 0.5 | turnip-like taste |
| (2)c. | A | 3.0 | burnt taste |
| (2)d. | A | 1.0 | coffee-like taste |
| (2)e. | A | 5.0 | sulfurous liver-like taste |
| (3)a. | B | 1.0 | earthy, sulfurous, paper-like taste |
| (3)a. | C | 1.08 | acid, sulfurous taste |
| (3)b. | B | 0.12 | bitter, peanut-like |
| (3)b. | C | 0.135 | ricy, iodoform-like |
| (3)c. | B | 0.20 | hazelnut, earthy taste |
| (3)c. | C | 0.22 | burnt cereal-like taste |
| (3)d. | B | 1.9 | earthy-like |
| (3)d. | C | 2.96 | burnt cereal, bitter, spicy |
| (3)e. | B | 1.0 | leathery, flowery taste |

TABLE XXXVI

| Number | Test | Quantity | Organoleptic Characterization |
|---|---|---|---|
| (1)a. | A | 3.0 | phenolic taste |
| (1)b. | A | 0.05 | phenolic, burnt taste |
| (1)c. | A | 0.01–0.05 | phenolic taste |
| (1)c. | C | 0.027 | solvent-like |
| (1)d. | A | 0.01 | burnt taste |
| (1)d. | C | 0.027 | phenolic |
| (1)e. | A | 0.01 | cresolic taste |
| (1)f. | A | 0.01 | burnt taste |
| (1)f. | B | 0.02–0.04 | roasted, dark flavor |
| (1)g. | A | 0.01 | phenolic taste |
| (1)h. | A | 0.02 | sweet, burnt taste |
| (1)h. | B | 0.09 | coffee, coffee grounds note |
| (1)i. | A | 0.1–0.2 | slightly burnt taste |
| (1)j. | A | 0.15 | balsam taste |
| (1)j. | B | 0.1 | coffee grounds note |
| (1)k. | A | 1.5 | tangerine taste |
| (1)l. | A | 1.0 | phenolic note |
| (1)m. | A | 1.0 | phenolic note |
| (1)n. | A | 6.0 | phenolic note |
| (2)a. | A | 1.0 | burnt, coffee taste |
| (2)a. | B | 1.0 | wood flavor note |
| (2)b. | A | 0.01 | coffee grounds note |
| (2)c. | A | 2.0 | phenolic note |
| (2)d. | A | 5.0 | phenolic note |
| (3)a. | A | 0.05–0.1 | burnt taste |
| (3)a. | B | 0.1–0.2 | smoky roasted flavor |
| (3)b. | A | 1.0 | weak earthy note |
| (4)a. | A | 0.25–0.5 | smoky taste |
| (4)a. | B | 0.4 | roasted, coffee grounds note |

TABLE XXXVII

| Number | Test | Quantity | Organoleptic Characterization |
|---|---|---|---|
| (1)a. | A | 5.0 | slightly green taste |
| (1)b. | A | 3.0 | burnt, caramel, slightly buttery taste |

TABLE XXXVIII

| Number | Test | Quantity | Organoleptic Characterization |
|---|---|---|---|
| (1)a. | A | 0.1–1.0 | onion, garlic taste |
| (1)b. | A | 0.25–0.5 | green, burnt coffee taste |
| (1)b. | B | 0.4 | aromatic note |
| (1)b. | C | 0.27 | sulfury note |
| (2)a. | A | 5.0 | slightly bland taste |
| (2)b. | A | 0.25 | garlic, earthy taste |
| (2)b. | B | 0.04 | roasted, natural coffee taste |
| (2)b. | C | 0.027 | bitter |
| (2)c. | B | 0.025 | mushroom, paper-like |
| (2)c. | C | 0.405 | mushroom, earthy note |
| (3)a. | A | 1.0 | burnt coffee note |
| (3)a. | C | 0.625 | mercaptan note |
| (3)b. | B | 0.025 | green, sweet, fatty note |
| (3)b. | C | 0.027 | earthy mushroom note |
| (3)c. | A | 1.0 | cabbage, garlic taste |
| (4)a. | A | 0.1–0.2 | earthy, coffee grounds note |
| (4)b. | A | 0.5 | coffee-like |
| (4)b. | C | 0.42 | sulfury, rubbery |
| (5)a. | A | 1.0 | caramel, coumarin-like |
| (5)a. | B | 0.5–1.0 | aromatic, fresh note |
| (5)a. | C | 0.27 | nutty, bitter almond taste |

As has been stated above the compounds having utility in the concept of this invention may be added to substances in varying amounts to alter or to modify the flavor of the substance by masking or blanking out undesirable flavors, by enhancing or fortifying desirable flavor or flavor notes, or by adding to the original substance an entirely new and different flavor. As will also be apparent to those skilled in the art various mixtures or blends of the flavor agents described may be used to achieve a desired flavor or flavor note. If, for example, one wishes to enhance a certain flavor note, or group of flavor notes present in a substance such as coffee, one needs only mix together certain of the described flavor agents to obtain the desired result.

Following are three examples of mixtures that have been prepared in accordance with the inventive concept.

TABLE XXXIX

| Identification | Compound Name | Parts by weight Ex. 1 | Ex. 2 | Ex. 3 |
|---|---|---|---|---|
| VII (1) a | 2-methyl-3-ethyl-pyrazine | — | 40 | 20 |
| VII (1) i | 2,3-diethyl-pyrazine | — | — | 0.5 |
| VII (1) d | 2-methyl-3-isopropyl-pyrazine | 5 | 5 | 7.5 |
| XVII (1) b | 2-acetyl-pyrazine | — | 30 | 10 |
|  | 2-methyl-3-methylthio-pyrazine | 2 | — | 2 |
| XXXI (1) a | furfurylthiol acetate | 2 | 2 | 3 |
|  | furfuryl methyl sulfide | — | 1 | — |
| XX (1) a | 2-acetyl thiophene | — | 80 | — |
| XXXI (2) b | furfuryl propyl sulfide | — | 3 | 1 |
| XXXVIII (2) b | 2,6-dimethyl-γ-thiopyrone | 4 | 4 | 4 |
| XXX (1) a | 2-methoxybenzenethiol | — | 12 | 6 |
|  | 2-hydroxyphenyl methyl sulfide | 1 | 2 | 1.5 |
| XXXVI (1) i | 3,4-xylenol | 4 | 4 | 2 |
| XXXVI (1) k | 2-hydroxyacetophenone | — | — | 5 |
| XXXVI (3) a | 4-ethyl-2-methoxy-phenol | — | 5 | 2.5 |
| XXXVI (1) c | 4-ethyl-phenol | — | — | 0.5 |
|  | pyridine | 20 | 30 | 20 |
| III (2) e | 2-vinyl-benzofuran | 3 | 3 | 4 |
| XXXVI (4) a | 4-vinyl-1,2-dimethoxy-benzene | — | 40 | — |
| XXVI (1) a | furfuryl propionate | — | 50 | — |
|  | furfural | — | 100 | — |

When added to a commercially available soluble powdered coffee beverage these blends of flavor agents added flavor notes which enhanced the flavor of the soluble coffee in the direction of that of roasted and ground coffee which has been brewed into a coffee beverage.

In order to demonstrate the flavor modifying or enhancing effect of the compounds of this invention a base material having the following composition was prepared:

| Compound | Parts by weight |
|---|---|
| 3-methyl-cyclopentane-1,2-dione | 50 |
| furfuryl alcohol | 50 |
| furfural | 10 |
| diacetyl | 5 |
| acetylmethylcarbinol | 30 |
| benzyl alcohol | 100 |
| propylene glycol | 755 |
| | 1000 |

Compounds of Group XXXV (Pyrazine Sulfur Compounds) were added to this base in varying amounts and the resulting compound mixtures were used to enhance or modify the flavor of the following food products:

(a) A solution of milk sweetened with sugar, at a dosage level of 10 grams of the flavor composition per 100 kg.
(b) A prepared ice-cream, at a dosage level of 10–15 g. of flavor composition per 100 kg.
(c) A white cake mix, at a level of 20 g. per 100 kg. of finished cake
(d) A milk pudding, at a dosage level of 10–15 g. per 100 kg.
(e) A milk chocolate, at a dosage level of 25 g. per 100 kg.

The exact formulation of the various compound mixtures are set out in the TABLE XL below.

TABLE XL

| Identification | Compound Name | Parts by weight Examples | | | | | |
|---|---|---|---|---|---|---|---|
| | | 4 | 5 | 6 | 7 | 8 | 9 |
| XXXV (2) a | 2-pyrazinyl-ethyl-mercaptan | 100 | — | — | — | 50 | 50 |
| XXXV (2) b | 2-pyrazinyl-ethyl methyl sulfide | — | 30 | — | — | — | 5 |
| XXXV (2) o | 2-pyrazinyl-ethyl ethyl sulfide | — | — | 125 | — | — | 20 |
| XXXV (2) d | 2-pyrazinyl-ethyl furfuryl sulfide | — | — | — | 100 | 50 | 35 |
| | 3-methyl-cyclopentane-1,2-dione | 50 | 50 | 50 | 50 | 50 | 50 |
| | furfuryl alcohol | 50 | 50 | 50 | 50 | 50 | 50 |
| | furfuryl | 10 | 10 | 10 | 10 | 10 | 10 |
| | diacetyl | 5 | 5 | 5 | 5 | 5 | 5 |
| | acetylmethyl carbinol | 30 | 30 | 30 | 30 | 30 | 30 |
| | benzyl alcohol | 100 | 100 | 100 | 100 | 100 | 100 |
| | propylene glycol | 655 | 725 | 630 | 655 | 655 | 655 |
| | | 1000 | 1000 | 1000 | 1000 | 1000 | 1000 |

All of the compounds of Examples 4–9 gave a resulting flavor modification in the food products which was organoleptically characterized as adding a definite roasted coffee flavor note.

A number of the Compounds of Group VII (Pyrazine Hydrocarbons) were added to the above described base material. The resulting compound mixtures had the formulations shown in TABLE XLI below.

TABLE XLI

| Identification | Compound Name | Parts by weight Examples | | | | | | | |
|---|---|---|---|---|---|---|---|---|---|
| | | 10 | 11 | 12 | 13 | 14 | 15 | 16 | 17 |
| VII (1) h | 2,3-dimethyl-pyrazine | 250 | — | — | — | — | — | 50 | — |
| VII (1) a | 2-methyl-3-ethyl-pyrazine | — | 25 | — | — | — | 20 | 15 | 10 |
| VII (1) c | 2-methyl-3-propyl-pyrazine | — | — | 45 | — | — | 25 | — | 15 |
| VII (1) d | 2-methyl-3-isopropyl-pyrazine | — | — | — | 45 | — | — | — | 20 |
| VII (1) i | 2-ethyl-3-ethyl-pyrazine (10% soln.) | — | — | — | — | 10 | — | 5 | 2 |
| | 3-methyl-cyclopentane-1,2-dione | 50 | 50 | 50 | 50 | 50 | 50 | 50 | 50 |
| | furfuryl alcohol | 50 | 50 | 50 | 50 | 50 | 50 | 50 | 50 |
| | furfuryl | 10 | 10 | 10 | 10 | 10 | 10 | 10 | 10 |
| | diacetyl | 5 | 5 | 5 | 5 | 5 | 5 | 5 | 5 |
| | acetylmethylcarbinol | 30 | 30 | 30 | 30 | 30 | 30 | 30 | 30 |
| | benzyl alcohol | 100 | 100 | 100 | 100 | 100 | 100 | 100 | |
| | propylene glycol | 505 | 730 | 710 | 710 | 745 | 710 | 685 | 708 |
| | | 1000 | 1000 | 1000 | 1000 | 1000 | 1000 | 1000 | 1000 |

When added to the same food products at the same dosage levels as described in connection with the Examples of TABLE XL above, the compound mixtures of Examples 10–17 imparted a pronounced nutty, green, fresh, earthy flavor note, with a light note of coffee grounds, to the foods.

Further compound mixtures utilizing mixtures of compounds from Group XXXV (Pyrazine Sulfur Compounds) and from Group VII (Pyrazine Hydrocarbons) were made as set out in TABLE XLII below.

TABLE XLII

| Identification | Compound Name | Parts by weight Examples | | | |
|---|---|---|---|---|---|
| | | 18 | 19 | 20 | 21 |
| XXXV (2) c | 2-pyrazinyl-ethylmercaptan | 20 | 20 | 20 | 20 |

TABLE XLII-continued

| Identification | Compound Name | Parts by weight Examples | | | |
|---|---|---|---|---|---|
| | | 18 | 19 | 20 | 21 |
| XXXV (2) d | 2-pyrazinyl-ethyl furfuryl sulfide | 20 | 20 | 20 | 20 |
| VII (1) a | 2-methyl-3-ethyl-pyrazine | — | — | 10 | 10 |
| VII (1) c | 2-methyl-3-propyl-pyrazine | — | — | 20 | 5 |
| VII (1) i | 2,3-diethyl-pyrazine (10% solution) | — | 10 | — | 5 |
| | 3-methyl-cyclopentane-1,2-dione | 50 | 50 | 50 | 50 |
| | furfuryl alcohol | 50 | 50 | 50 | 50 |
| | furfuryl | 10 | 10 | 10 | 10 |
| | diacethyl | 5 | 5 | 5 | 5 |
| | acetylmethylcarbinol | 30 | 30 | 30 | 30 |
| | benzyl alcohol | 100 | 100 | 100 | 100 |
| | propylene glycol | 715 | 705 | 685 | 69539 |
| | | 1000 | 1000 | 1000 | 1000 |

When added to the same food products as above and in the same dosage levels, the foods were found to have their flavor modified to one with a definite coffee flavor with a light touch of a coffee grounds note.

Some further compound mixtures were prepared from compounds of Group VII (Pyrazine Hydrocarbons) using as a base the following mixture:

| | Parts by weight |
|---|---|
| 3-methyl-cyclopentane-1,2-dione | 200 |
| Essence of cinnamon | 10 |
| Essence of sweet fennel | 20 |
| Essence of star anise | 20 |
| benzyl alcohol | 250 |
| propylene glycol | 500 |
| | 1000 |

The exact formulations of these compound mixtures are set out in TABLE XLIII below.

TABLE XLIII

| Identification | Compound Name | Parts by weight Examples | | | | |
|---|---|---|---|---|---|---|
| | | 22 | 23 | 24 | 25 | 26 |
| VII (1) e | 2-methyl-3-butyl-pyrazine | 25 | — | — | — | 5 |
| VII (1) b | 2-methyl-3-isobutyl-pyrazine | — | 50 | — | — | 15 |
| VII (1) f | 2-methyl-3-amyl-pyrazine | — | — | 100 | — | 20 |
| VII (1) g | 2-methyl-3-hexyl-pyrazine | — | — | — | 50 | 15 |
| | 3-methyl-cyclopentane-1,2-dione | 200 | 200 | 200 | 200 | 200 |
| | Essence of cinnamon | 10 | 10 | 10 | 10 | 10 |
| | Essence of sweet fennel | 20 | 20 | 20 | 20 | 20 |
| | Essence of star anise | 20 | 20 | 20 | 20 | 20 |
| | benzyl alcohol | 250 | 250 | 250 | 250 | 250 |
| | propylene glycol | 475 | 450 | 400 | 450 | 445 |
| | | 1000 | 1000 | 1000 | 1000 | 1000 |

When added to a soft gum-drop candy formulation at a dosage level of 30 g. per 100 kg., to an ice-cream mix at a dosage level of 8-10 g. per 100 kg., to a milk pudding mix at a dosage level of 8-10 g. per 100 kg., and to a hard candy formulation at a dosage level of 15-20 g. per 100 kg., the compound mixtures imparted a definite anise, liquorice-like flavor note to the finished products.

It should be kept in mind, as will be appreciated by those skilled-in-the-art, that with many flavors it is possible to imitate the natural flavor by selecting a limited number of the flavor enhancing substances examplified above. Coffee aroma, on the other hand, is much more complex than the ordinary flavoring materials and may necessitate the combination of many more of the examplified ingredients for reproduction.

It will also be understood that whereas the preferred embodiment of this invention is directed toward the enhancement or modification of coffee flavors, the concept of the invention has much wider application. While some of the compounds may be characterized by terms which are not directly related to coffee flavors, these compounds, when used in more complex formulae, may contribute desirable flavor notes to the overall flavor and aroma.

To summarize briefly this invention relates to a group of chemical compounds which have been found to have utility for the alteration or modification of the flavor of other materials. These compounds, called flavor agents or flavor modifiers, may be used in minute quantities to enhance the natural flavor of substances to which they are added, or to alter or modify a flavor which is undesirable, or to impart to a substance additional or different flavors or flavor notes. The flavor agents of the invention are used in minor, but flavor altering amounts, in any case, in quantities sufficient to obtain the desired results. The flavor modifiers are of particular importance and usefulness in the modification, alteration or enhancement of the flavor of coffee beverages made from soluble coffee and the preferred embodiment of the invention contemplates their use in conjunction with such products.

The flavor agents of the invention may be added at a convenient step in the soluble coffee process such as plating the dried soluble coffee with a desired dilution of the flavor agent in an acceptable solution followed by drying. In certain instances the desired agent may be added directly to a concentrated coffee extract and the mixture dried into a soluble coffee product which contains the flavor agent as an integral part thereof. Other methods of incorporation of the agents will suggest themselves to those skilled in the art and may, of course, be used without departing from the inventive concept, which may be described as being a composition of matter comprising a combination of a soluble coffee product, however prepared, whether liquid or solid, concentrated or dilute, which contains combined therewith a minor, but flavor modifying amount, of a flavor agent as described herein.

What is claimed is:

1. Pyridine sulfur compounds selected from the group consisting of (pyridyl-2)-methyl ethyl sulfide and (pyridyl-2)-methanethiol acetate.

2. A pyridine sulfur compound as in claim 1 in which said compound is (pyridyl-2)-methyl ethyl sulfide.

3. A pyridine sulfur compound as in claim 1 in which said compound is (pyridyl-2)-methanethiol acetate.

* * * * *

UNITED STATES PATENT AND TRADEMARK OFFICE
CERTIFICATE OF CORRECTION

PATENT NO. : 4,126,618
DATED : November 21, 1978
INVENTOR(S) : Max Winter, et al.

It is certified that error appears in the above-identified patent and that said Letters Patent is hereby corrected as shown below:

On the title page:

[75] Inventors:, after "Switzerland",
insert --, Irving M. Goldman, Niantic, Conn. --

Related U.S. Application Data
[60], after "3,702,253, which is a continuation",
delete "-in-part".

Signed and Sealed this

Twenty-ninth Day of June, 1993

*Attest:*

*Attesting Officer*

MICHAEL K. KIRK

*Acting Commissioner of Patents and Trademarks*